(12) United States Patent
He et al.

(10) Patent No.: US 7,489,400 B1
(45) Date of Patent: Feb. 10, 2009

(54) SYSTEM AND METHOD OF APPLYING XENON ARC-LAMPS TO PROVIDE 193 NM WAVELENGTHS

(75) Inventors: Ping He, Lincoln, NE (US); Martin M. Liphardt, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 322 days.

(21) Appl. No.: 11/497,921

(22) Filed: Aug. 3, 2006

Related U.S. Application Data

(63) Continuation-in-part of application No. 10/613,051, filed on Jul. 7, 2003, now Pat. No. 7,099,006, and a continuation-in-part of application No. 09/945,962, filed on Sep. 4, 2001, now Pat. No. 7,075,649, and a continuation-in-part of application No. 09/517,125, filed on Feb. 29, 2000, now abandoned, and a continuation-in-part of application No. 09/246,888, filed on Feb. 8, 1999, now Pat. No. 6,084,675, and a continuation-in-part of application No. 09/232,257, filed on Jan. 19, 1999, now Pat. No. 6,141,102, and a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/225,371, filed on Jan. 4, 1999, now Pat. No. 6,100,981, and a continuation-in-part of application No. 09/225,076, filed on Jan. 4, 1999, now Pat. No. 5,963,325, application No. 09/246,888, which is a continuation-in-part of application No. 08/912,211, filed on Aug. 15, 1997, now Pat. No. 5,872,630, which is a continuation-in-part of application No. 08/618,820, filed on Mar. 20, 1996, now Pat. No. 5,706,212, and a continuation-in-part of application No. 08/530,892, filed on Sep. 20, 1995, now Pat. No. 5,666,201, application No. 11/497,921, and a continuation-in-part of application No. 11/084,827, filed on Mar. 21, 2005, now Pat. No. 7,301,631, and a continuation-in-part of application No. 10/928,429, filed on Aug. 27, 2004, now Pat. No. 7,317,529, and a continuation-in-part of application No. 10/699,540, filed on Nov. 1, 2003, now Pat. No. 7,158,231, and a continuation-in-part of application No. 10/613,051, filed on Jul. 4, 2003, now Pat. No. 7,099,006, and a continuation-in-part of application No. 10/425,801, filed on Apr. 29, 2003, now Pat. No. 6,930,813, and a continuation-in-part of application No. 09/583,229, filed on May 30, 2000, now Pat. No. 6,804,004, and a continuation-in-part of application No. 09/419,794, filed on Oct. 18, 1999, now Pat. No. 6,549,282.

(60) Provisional application No. 60/229,755, filed on Sep. 5, 2000, provisional application No. 60/473,615, filed on May 28, 2003, provisional application No. 60/473,616, filed on May 28, 2003, provisional application No. 60/553,032, filed on Mar. 15, 2004, provisional application No. 60/517,566, filed on Nov. 6, 2003, provisional application No. 60/572,204, filed on May 18, 2004, provisional application No. 60/527,554, filed on Dec. 6, 2003, provisional application No. 60/527,638, filed on Dec. 8, 2003, provisional application No. 60/576,466, filed on Jun. 3, 2004, provisional application No. 60/498,479, filed on Aug. 28, 2003, provisional application No. 60/611,173, filed on Sep. 17, 2004, provisional application No. 60/749,768, filed on Dec. 13, 2005.

(51) Int. Cl.
*G01J 4/00* (2006.01)

(52) U.S. Cl. .................................................. 356/369

(58) Field of Classification Search ......... 356/364–369; 250/225
See application file for complete search history.

(56) References Cited

U.S. PATENT DOCUMENTS 5,382,804 A 1/1995 D'Silva .................. 250/493.1

(Continued)

*Primary Examiner*—Hoa Q Pham
(74) *Attorney, Agent, or Firm*—James D. Welch

(57) ABSTRACT

Application of Xenon arc-lamps to provide UV/deep UV wavelengths in spectrophotometer, reflectometer, ellipsometer, polarimeter or the like systems.

28 Claims, 10 Drawing Sheets

U.S. PATENT DOCUMENTS

| | | | |
|---|---|---|---|
| 5,666,201 A | 9/1997 | Johs et al. | 356/369 |
| 5,872,630 A | 2/1999 | Johs et al. | 356/369 |
| 6,268,917 B1 | 7/2001 | Johs | 356/369 |
| 6,753,961 B1 | 6/2004 | Norton et al. | 356/364 |
| 6,762,824 B2 | 7/2004 | Mori | 355/52 |
| 6,862,090 B2 | 3/2005 | Chen et al. | 356/300 |
| 6,868,223 B2 | 3/2005 | Shinoda | 385/146 |
| 7,359,052 B2 * | 4/2008 | Fielden et al. | 356/369 |
| 2002/0008874 A1 * | 1/2002 | Lee et al. | 356/369 |

* cited by examiner

SYSTEM AND METHOD OF APPLYING XENON ARC-LAMPS TO PROVIDE 193 NM WAVELENGTHS

This application is a CIP of Allowed application Ser. No. 10/613,051 Filed Jul. 7, 2003, (now U.S. Pat. No. 7,099,006); and therevia claims benefit of 60/229,755 filed Sep. 5, 2000. This application is also a Continuation-in-Part of application Ser. No. 09/945,962 Filed Sep. 4, 2001, (now U.S. Pat. No. 7,075,649), and therevia of application Ser. No. 09/517,125 Filed Feb. 29, 2000, (now abandoned); and of Ser. No. 09/246,888 filed Feb. 8, 1999, (now U.S. Pat. No. 6,084,675); and further of Ser. No. 09/225,118 filed Jan. 4, 1999 (now U.S. Pat. No. 6,084,674); Ser. No. 09/223,822 filed Jan. 4, 1999 (now U.S. Pat. No. 6,118,537); Ser. No. 09/232,257 filed Jan. 19, 1999 (now U.S. Pat. No. 6,141,102); Ser. No. 09/225,371 filed Jan. 4, 1999 (now U.S. Pat. No. 6,100,981); Ser. No. 09/225,076 filed Jan. 4, 1999 (now U.S. Pat. No. 5,963,325); which applications depended from Ser. No. 08/997,311 filed Dec. 23, 1997, (now U.S. Pat. No. 5,946,098). Further, via the Ser. No. 09/246,888 application, this application is a Continuation-In-Part of Ser. No. 08/912,211 filed Aug. 15, 1997, (now U.S. Pat. No. 5,872,630), which Continued-In-Part from Ser. No. 08/530,892 filed Sep. 20, 1995, (now U.S. Pat. No. 5,666,201); and and is also a CIP of Ser. No. 08/618,820 filed Mar. 20, 1996, (now U.S. Pat. No. 5,706,212). In addition, priority is claimed from Ser. No. 09/162,217 filed Sep. 29, 1998 via above applications. This application is further a CIP of application Ser. No. 10/928,429 Aug. 27, 2004 now U.S. Pat. No. 7,317,529 and therevia claims Benefit of Provisional Application Ser. No. 60/473,615 Filed May 28, 2003. This application is a further a CIP of application Ser. No. 09/583,229 filed May 30, 2000, U.S. Pat. No. 6,804,004 and therevia of Ser. No. 09/419,794 filed Oct. 18, 1999 (now U.S. Pat. No. 6,549,282); Ser. No. 10/613,051 Filed Jul. 7, 2003, (now U.S. Pat. No. 7,099,006); Ser. No. 10/699,540 Filed Nov. 1, 2003, (now U.S. Pat. No. 7,158,231); Ser. No. 10/425,801 Filed Apr. 29, 2003, (now U.S. Pat. No. 6,930,813); and claims Benefit, therevia or directly, of Provisional Applications 60/473,616 Filed May 28, 2003; (via the 540 application); 60/553,032 Filed Mar. 15, 2004; 60/517,566 Filed Nov. 6, 2003; 60/572,204 Filed May 18, 2004; 60/527,554 Filed Dec. 6, 2003; 60/527,638 Filed Dec. 8, 2003; 60/576,466 Filed Jun. 3, 2004; 60/498,479 Filed Aug. 28, 2003. This application is a further a CIP of application Ser. No. 11/084,827, (now U.S. Pat. No. 7,301,631) Filed Mar. 21, 2005 and therevia claims Benefit of Provisional Ser. No. 60/611,173 Filed Sep. 17, 2004. This application further claims benefit of Provisional Application Ser. No. 60/749,768 Filed Dec. 13, 2005.

TECHNICAL FIELD

The present invention relates to sources of electromagnetic radiation and more particularly to application of Xenon arc-lamps to provide UV/deep UV (eg. 193 nm), wavelengths with application in reflectometer, spectrophotometer, ellipsometer, polarimeter or the like systems.

BACKGROUND

It is known to apply arc-lamps in spectrophotometer, reflectometer, ellipsometer, polarimeter or the like systems which direct beams of spectroscopic electromagnetic radiation therefrom to samples at normal or oblique angles-of-incidence. Where a wide range of wavelengths is required, (eg. IR through Visible and UV), however, it is conventional practice to provide multiple sources of electromagnetic radiation. For instance, while Xenon lamps are commonly used to provide Visible wavelengths, they have not been generally applied to provide, for example, 193 nm. Typical practice is to combine said Xenon lamps with, for instance, a Deuterium lamp to provide the shorter wavelengths. This requires supporting the multiple sources.

Known Patents which are relevant are:
U.S. Pat. No. 6,862,090 to Chen et al.;
U.S. Pat. No. 6,762,824 to Mori;
U.S. Pat. No. 6,868,223 to Shinoda;
U.S. Pat. No. 6,753,961 to Norton et al.;
U.S. Pat. No. 6,583,877 to Norton;
U.S. Pat. No. 6,268,917 to Johs;
U.S. Pat. No. 7,027,158 to Hendrix et al.

It would therefore be of benefit if a single Xenon lamp, (eg. which operates at a wattage of less than 500 watts), could be utilized to provide UV/deep UV (eg. 193 nm), wavelengths, and the present invention provides numerous insights as to how said benefit can be realized.

DISCLOSURE OF THE INVENTION

Ellipsometry provides a technique for determining the Dielectric Constant as well as physical properties of samples. Basically, electromagnetic radiation, which can be monochromatic or spectroscopic, of a known polarization state is caused to interact with a sample, reflect from or transmit therethrough and enter a detector wherein the polarization state is monitored. Changes in polarization state are at least partially attributable to interaction with the sample and are expressed as sample PSI ($\psi$) and DELTA ($\Delta$) for a particular angle-of-incidence (AOI) and Wavelength, as defined by:

$$\rho = rp/rs = \operatorname{Tan}(\Psi) \exp(i\Delta)$$

where rp and rs are orthogonal components of a beam of electromagnetic radiation in a plane perpendicular to the sample surface, and parallel thereto, respectively. For the purposes of the invention in this disclosure, the ellipsometer can be of any functional type, such as:

nulling;
rotating analyzer;
rotating polarizer;
rotating compensator;
modulation element;
and functional equivalents.

The disclosed invention provides, in the context of ellipsometer and the like systems, means for producing, directing, conditioning, and impinging spectroscopic electromagnetic radiation onto a spot of a sample, and comprises selections from the group consisting of:

source means for producing desired electromagnetic radiation wavelength content;
means for reliably directing electromagnetic radiation emitted from a source thereof in a common beam direction;
means for emphasizing relative intensity of electromagnetic radiation emitted by a source at wavelengths in desired ranges, and specifically at 193 nm.

It is noted that a material system investigation system to which the present invention can be applied can comprise a Xenon source of a polychromatic beam of electromagnetic radiation, a polarizer, a material system supporting stage, an analyzer and a detector, and a processor for performing calculations that evaluate detector output signal, there optionally being present at least one compensator between said polarizer and analyzer.

Electromagnetic Beam Source

The present invention is found in the use of a Xenon arc-lamp to provide a 193 nm wavelength. This is not conventionally done as the intensity of longer wavelengths provided by a Xenon arc-lamp (ie. in the Visible range), are much greater. Detectors set to detect them are relatively insensitive to the lower intensity at 193 nm, and generally if detector gain is stepped-up, the detector circuitry saturates. Said present invention approach can be as simple as providing a Xenon arc-lamp rated at relatively high wattage, (eg. 150 Watt), as a source which directly provides 193 nm electromagnetic radiation, or can involve means for enhancing the intensity at said 193 nm.

Again, it is to be understood that the present invention finds application in spectrophotometer, reflectometer, ellipsometer, polarimeter or the like systems. Such systems comprise means for generating a polychromatic beam of electromagnetic radiation with a desired wavelength content, for application in a material system investigation system. An ellipsometer system, for instance, comprises said source of a polychromatic beam of electromagnetic radiation, a polarizer means for imposing a state of polarization, a material system supporting stage, an analyzer means for detecting specific states of polarization, and a detector means which can direct different wavelengths into different detectors. Said material system investigation system can optionally comprise at least one compensator and/or aperture placed ahead of, and/or after said material system supporting stage, and when said compensator is present the system is properly termed a polarimeter. Also present is a processor for performing calculations that evaluate detector means intensity output signal. Where polarizer, analyzer and compensators are absent the system is a spectrophotometer or reflectometer.

In use said source of a polychromatic beam of electromagnetic radiation is caused to provide a beam of electromagnetic radiation and direct it to interact with a sample which is placed on said material system supporting stage after passing through said polarizer means, and then proceed through said analyzer means and into said detector means, which in turn produces data corresponding to intensity vs. angle-of-incidence and/or wavelength.

While not limiting, the material system investigation system can comprise apertures, (eg. at least four apertures between the source of a polychromatic beam of electromagnetic radiation and the material system supporting stage, and at least three apertures between the material system supporting stage and the detector means), through which the beam passes.

A present invention system can include a system for providing an output beam of polychromatic electromagnetic radiation which has a relatively broad and flattened intensity vs. wavelength characteristic over a wavelength spectrum, said output beam of polychromatic electromagnetic radiation substantially being a commingled composite of a plurality of input beams of polychromatic electromagnetic radiation which individually do not provide as relatively broad and flattened an intensity vs. wavelength characteristic over said wavelength spectrum as does said output commingled composite beam of polychromatic electromagnetic radiation. Said system comprises:

a. at least a first Xe source of polychromatic electromagnetic radiation; and
  b. at least a first electromagnetic beam combining means.

The at least a first electromagnetic beam combining means is positioned with respect to said Xe source of polychromatic electromagnetic radiation such that a first beam of polychromatic electromagnetic radiation from said Xe source of polychromatic electromagnetic radiation passes through said at least a first electromagnetic beam combining means, and such that a second beam of polychromatic electromagnetic radiation, also from said Xe source of polychromatic electromagnetic radiation, reflects from said at least a first electromagnetic beam combining means and is commingled with said first beam of polychromatic electromagnetic radiation from said Xe source of polychromatic electromagnetic radiation which passes through said at least a first electromagnetic beam combining means. There can be filters present in both beams which serve to attenuate the intensity of the visible wavelengths. The resultant beam of polychromatic electromagnetic radiation is substantially the output beam of polychromatic electromagnetic radiation which has a relatively broad and flattened intensity vs. wavelength over a wavelength spectrum and comprises the commingled composite of the plurality of input beams of polychromatic electromagnetic radiation which individually do not provide such a relatively broad and flattened intensity vs. wavelength over a wavelength spectrum characteristic. The present invention system for providing an output beam of polychromatic electromagnetic radiation which has a relatively broad and flattened intensity vs. wavelength characteristic over a wavelength spectrum optionally further comprises a second electromagnetic beam combining means. When present, the second electromagnetic beam combining means is positioned with respect to said commingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to a third beam from said Xe source of polychromatic electromagnetic radiation, but such that said third beam of electromagnetic radiation from said Xe source of polychromatic electromagnetic radiation reflects from said second electromagnetic beam combining means such that a second resultant beam of polychromatic electromagnetic radiation is produced which is substantially an output beam of polychromatic electromagnetic radiation which has a relatively even more broadened and flattened intensity vs. wavelength over a wavelength spectrum, comprising a commingled composite of a plurality of input beams of polychromatic electromagnetic radiation from said first, second and third beams from said Xe source. Again, filters can be present in the pathway of said third beam from said first source which attenuate the intensity of the Visible wavelengths.

Further, at least one of said first and second, (when present), electromagnetic beam combining means can be pivotally mounted in said system for providing an output beam of polychromatic electromagnetic radiation which has a relatively broad and flattened intensity vs. wavelength characteristic over a wavelength spectrum to allow rotation thereof, said rotation serving to commingle and direct transmitted and reflected beams of electromagnetic radiation along a common locus. Where the beams of electromagnetic radiation can be moved, as where they are carried by an optical fiber, said pivoting capability might not be required but would allow adjusting the angle at which beams of polychromatic electromagnetic radiation passes through and reflect from said at least one electromagnetic beam combining means. This allows control of the relative amounts of transmission and reflection effected by an electromagnetic beam combining means.

It is further known that arc-lamps generally present with an elongated dimension. Manufacturer recommendation is usually that arc-lamps be mounted so that their elongated dimension is oriented vertically. The problem this presents in application to spectrophotometer, reflectometer, ellipsometer, polarimeter or the like systems is that as an arc-lamp ages, the focal point from which a beam of electromagnetic radiation therefrom originates moves. This effectively changes the angle-of-incidence of the beam to a sample surface. As said angle-of-incidence must be known to enable valid analysis of data corresponding to reflected or transmitted electromagnetic radiation from or through said sample, it can be appreciated that where arc-lamps are mounted with their elongated dimension oriented vertically in spectrophotometer, reflectometer, ellipsometer, polarimeter or the like systems, problems present. One solution is to use a sequence of mirrors to rotate the locus of the elongated dimension of an arc-lamp 90 degrees. Then as the focal point origin of the beam changes, the angle-of-incidence does not change. Rather a the beam impinges on a sample surface at a laterally slightly different point. Another approach is to ignore manufacturer recommendations and mount the arc-lamp so that elongated dimension thereof projects horizontally. However, when this is done it is found that the upper inner surface of the arc-lamp becomes progressively less transparent because of sputtered depositions thereon. The lower inner surface of the horizontally oriented arc-lamp, however, remains relatively unaffected. One aspect of the present invention is based in a common need to be able to easily provide more than one angle-of-incidence of a beam of electromagnetic radiation to a sample surface, when obtaining data using a spectrophotometer, reflectometer, ellipsometer, polarimeter or the like systems. And the present invention is further based in the fact that where the source of the beam of electromagnetic radiation is a Xenon arc-lamp with an elongated dimension thereof oriented horizontally, it is necessary to take precautions to assure that said beam exits a relatively clear lower inner surface of the horizontally oriented arc-lamp, which remains relatively unaffected over time of usage.

In an alternative approach, the present invention then provides that electromagnetic radiation be obtained from the lower inner surface of a horizontally oriented arc-lamp, and that a reflective means be applied to direct said beam to a sample surface. When the angle-of-incidence of the beam with respect to said sample surface is to be changed, the vertical height of the horizontally oriented arc-lamp and reflective mans is changed simultaneously with rotating the reflective means to change the angle said beam reflects from said reflective means. This results in a beam of electromagnetic radiation always exiting the lower inner surface of the horizontally oriented arc-lamp, and progressing to reflect from said reflective means and impinge on the surface of the sample at substantially the same position thereon, no matter what angle-of-incidence is chosen. A simpler approach provides a reflective means below a horizontally mounted Xenon arc-lamp which can be raised and lowered as well as rotated. A beam from the Xenon arc-lamp can then be directed to a sample by said reflective means, without a combined vertical motion of the Xenon arc-lamp itself.

Beam Directing

The disclosed invention also allows that a beam of electromagnetic radiation can be produced by applying a back-reflector which is positioned to redirect electromagnetic radiation produced by a source thereof which is emitted in a direction other than in the direction of the beam, (ie. substantially 180 degrees opposite that of a desired beam). A disclosed system for improving characteristics of a spectroscopic beam of electromagnetic radiation directed in a "forward" direction from a source of electromagnetic radiation directing can comprise:

an off-axis parabolic mirror; and
a flat reflecting means;

said off-axis parabolic mirror being positioned to receive electromagnetic radiation from said source, and being positioned substantially in a "backward" projection direction 180 degrees rotated from said "forward" direction, and said flat reflecting means being positioned to receive electromagnetic radiation which reflects from said off-axis parabolic mirror and via reflection direct it directly back to said off-axis parabolic mirror, which off-axis parabolic mirror then directs it back through said source of electromagnetic radiation and along said "forward" direction;

the effect being increased intensity in said "forward" directed beam.

The flat reflecting means can uniformly reflect all wavelengths.

The flat reflecting means can reflect different wavelengths with different efficiencies.

The flat reflecting means can reflect IR and UV wavelengths more efficiently than visual range wavelengths.

The flat reflecting means can comprise semiconductor.

The flat reflecting means can comprise silicon.

The flat reflecting means can comprise silicon with a thin film of other material on its reflective surface, and a typical non-limiting material on said reflective surface is SiO2.

A variation of the system for improving characteristics of a spectroscopic beam of electromagnetic radiation directed in a "forward" direction from a source of electromagnetic radiation directing comprises:

a concave mirror;

said concave mirror being positioned to receive electromagnetic radiation from said source, and being positioned substantially in a "backward" projection direction 180 degrees rotated from said "forward" direction;

such that electromagnetic radiation from said source thereof which is directed in the "backward" direction is reflected from said concave mirror in a "forward" direction;

the effect being increased intensity in said "forward" directed beam.

The concave mirror can comprise semiconductor, such as silicon, or silicon with a thin film of other material on its reflective surface, (eg. a typical non-limiting material is SiO2).

Another variation of a system for improving characteristics of a spectroscopic beam of electromagnetic radiation directed in a "forward" direction from a source of electromagnetic radiation directing comprises:

a flat reflecting means; and
a spherical mirror;

said flat reflecting means being positioned to receive electromagnetic radiation from said source, and being positioned substantially in a "backward" projection direction 180 degrees rotated from said "forward" direction, and said spherical mirror being positioned to receive electromagnetic radiation which reflects from said flat reflecting means and via reflection direct it directly back to said flat reflecting means, which flat reflecting means then directs it back through said source of electromagnetic radiation and along said "forward" direction; the effect being increased intensity in said "forward" directed beam.

The flat reflecting means can uniformly reflect all wavelengths, or can reflect different wavelengths with different efficiencies, (eg. reflect IR and UV wavelengths more efficiently than visual range wavelengths), or can comprise semiconductor, (eg. silicon, or silicon with a thin film of other material on its reflective surface such as SiO2).

While Back-reflectors are beneficial, it has been found that over time they can become less efficient as a result of deposits onto the reflective surface thereof. Another aspect of the present invention provides that a back-reflector be placed into a container which has openings present to allow the flow of gas into, through and out thereof, as well as allow electromagnetic radiation to enter thereinto and exit therefrom. It has been found that the gas flow prevents accumulation of deposits onto the back-reflector surface.

A present invention system for providing a beam of electromagnetic radiation can be described as comprising:

a source of electromagnetic radiation; and a back-reflector having a reflective surface;

said back-reflector being situated with respect to said source of electromagnetic radiation such that at least some electromagnetic radiation emitted in a direction other than that of the beam of electromagnetic radiation, is redirected into the direction of said beam of electromagnetic radiation thereby;

said system being characterized in that said back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

As applied in an ellipsometer system, the present invention can be described as comprising a source of electromagnetic radiation, a polarizer, a stage for supporting a sample, an analyzer and a detector, there optionally being at least one compensator present between said polarizer and stage and/or between said stage and analyzer;

such than in use a beam of electromagnetism is caused to be directed by said source thereof toward a sample placed on said stage, interact with said sample, pass through said analyzer and enter said detector, said beam also passing through any present compensator, said source of electromagnetic radiation comprising a back-reflector having a reflective surface, said back-reflector being situated in said source of electromagnetic radiation such that at least some electromagnetic radiation emitted in a direction other than that of the beam of electromagnetic radiation, is redirected into the direction of said beam of electromagnetic radiation thereby; said back-reflector being in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

A method of characterizing a sample comprises the steps of:

a) providing an ellipsometer system as just described;

b) placing a sample onto said stage;

c) simultaneously causing:

said source of electromagnetic radiation to provide a beam of electromagnetic radiation and direct it to pass through said polarizer, interact with said sample and enter said detector, and through any compensator present;

causing gas to flow into and out of said container;

and analyzing signals produced by said detector to characterize said sample.

Said system for investigating a sample can further comprise:

a) a polarizer between said source and sample; and b) an analyzer between said sample and detector;

and constitute an ellipsometer, and if a compensator is present between said source and detector, a polarimeter results.

Beam Directing and Conditioning

Another aspect of the disclosed invention addresses conditioning, as well as directing electromagnetic radiation produced by a source thereof along a desired locus. As already identified, a problem with many Sources of Electromagnetic Radiation is that they emit radiation along other than a desired beam path. Further, many Sources provide radiation of a relatively high intensity between the Ultraviolet and Infrared, but drop off quickly in the UV and IR. That is, generally, Sources of Electromagnetic Radiation often provide wavelength/intensity characteristics which are less than perfect for certain Ellipsometric applications.

One already identified approach is to improving the characteristics of a Source of Electromagnetic Radiation is to provide a back reflector, behind a source of electromagnetic radiation, which serves to direct electromagnetic radiation which exits the source in a useful forward direction. This increases Intensity generally. Based on the nature of the Back Reflector, however, it is possible to selectively enhance Intensity in some wavelengths as opposed to others.

For instance, it is possible to provide a reflecting means in the pathway of an electromagnetic beam, upon which reflecting means is a coating which emphasizes reflection of the UV, (eg. at 193 nm), relative to non-UV range wavelengths. An example of such a coating on a reflective means is 600 to 1200 Angstroms, for instance, of Silicon Dioxide on Silicon. This approach enables setting "gain" providing means at higher levels to emphasize UV signals, while not over amplifying, and even saturating higher intensity, (eg. Visible), wavelengths signals. Back Reflectors can be comprised of such reflective materials, and/or one or more separate reflecting elements can be placed in a Beam of Electromagnetic Radiation between a Source and Detector. Said material system investigation system can then be characterized in that there is present in the pathway of polychromatic beam at least one reflective element which reflects more efficiently in wavelength ranges in which the intensity from the source is less intense as compared to wavelengths in ranges in which the intensity from the source is of relatively higher intensity. In use said source of a polychromatic beam of electromagnetic radiation is caused to provide a beam of electromagnetic radiation which is directed to interact with a sample which is placed on said material system supporting stage, then after interaction with said sample enter into said detector, which in turn produces data corresponding to a parameter vs. angle-of-incidence or wavelength or mathematical equivalent, said polychromatic beam of electromagnetic radiation also being caused to reflect from said at least one reflective element at a point between said source of a polychromatic beam of electromagnetic radiation and said detector.

Another approach to improving optical element characteristics is to coat transmissive elements, such as lenses present in the system, to minimize entry and exit losses caused thereby, and improve overall UV transmission therethrough. An example is a single 300 Angstrom layer of $MgF_2$. Multi-layer coatings can also be used.

Another approach to conditioning electromagnetic beams is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

If attenuation of UV wavelengths thereby is not considered prohibitive, optical fibers can be applied. However, if optical fibers are utilized, to reduce loss of UV intensity at fiber entry, a narrow (eg. smaller that the fiber dimension), beam can be focused at the entry to the fiber.

It is also disclosed that the following approaches, which focus on increasing or concentrating the amount of UV electromagnetic radiation, can be practiced independently or in combination:

Utilize a source of electromagnetic radiation which emphasizes UV wavelength production. Various wattage lamps (eg. 35, 75 and 150 can be applied and where necessary can involve application of various indirect heat sink based cooling and produced ozone containment.

In the case of rotating compensator ellipsometers, reduce the rotation speed of the compensator so that for the same number of rotations more total electromagnetic radiation passes therethrough and reaches the detector.

Take multiple scans of data to improve signal to noise.

Combine the output of multiple pixels in a detector which receive UV radiation.

An approach which is focused on providing a small spot size, (eg. 35 mm), is to identify optical elements which enter dispersion of wavelengths entered thereinto and reduce their effect. Dispersion, it should be appreciated causes different wavelengths in electromagnetic radiation to focus at different points on a sample. Reduced dispersion can be accomplished by, for instance, adding optical elements which offset the effect entered by existing optical elements. While increasing physical dimensions and potentially adding entry and exit and transmission attenuation effects, the result can be a smaller spot size.

The disclosed invention provides sources of electromagnetic radiation which provide desired wavelength output; means for improving relative intensity of electromagnetic radiation emitted by a source at wavelengths in, for instance, IR ad UV ranges (eg. specifically 193 nm); means for directing electromagnetic radiation emitted by a source along a desired locus; and reflective imaging and focusing means for achromatically providing a small spot size of concentrated electromagnetic radiation where it is caused to impinge upon a sample surface.

PRESENT INVENTION

With the foregoing in mind, it is disclosed that the present invention can best described as a material system investigation system comprising a Xenon source of a polychromatic beam of electromagnetic radiation, a material system supporting stage, a detector, and a processor for performing calculations that evaluate detector output signal; there optionally being present a polarizer between said source and said material system supporting stage, an analyzer between said material system supporting stage and said detector, and optionally at least one compensator between said polarizer and analyzer. In use said Xenon source of a polychromatic beam of electromagnetic radiation is caused to provide a beam of electromagnetic radiation and direct it to interact with a sample which is placed on said material system supporting stage after optionally passing through said polarizer and analyzer and at least one compensator, and into said detector which in turn produces data corresponding to a parameter vs. angle-of-incidence and/or wavelength or mathematical equivalent. Said material system investigation system is characterized in that said source of a polychromatic beam of electromagnetic radiation comprises only at least one Xenon arc lamp which is used to provide 193 nm wavelength electromagnetic radiation without application of a supplemental source of electromagnetic radiation.

To aid with providing a good 193 nm signal, said Xenon source of a polychromatic beam of electromagnetic radiation can comprise:

a. at least a first Xenon source of polychromatic electromagnetic radiation; and b. at least a first electromagnetic beam combining means;

said at least a first electromagnetic beam combining means being positioned with respect to said first Xenon source of polychromatic electromagnetic radiation such that a beam of polychromatic electromagnetic radiation from said first Xenon source of polychromatic electromagnetic radiation passes through said at least a first electromagnetic beam combining means, and such that another beam of polychromatic electromagnetic radiation from said first Xenon source of polychromatic electromagnetic radiation reflects from said at least a first electromagnetic beam combining means and is commingled with said beam of polychromatic electromagnetic radiation from said first Xenon source of polychromatic electromagnetic radiation which passes through said at least a first electromagnetic beam combining means, said resultant beam of polychromatic electromagnetic radiation substantially being said output beam of polychromatic electromagnetic radiation which has an increased 193 nm intensity. Said system for providing an output beam of polychromatic electromagnetic radiation which has a relatively broad and flattened intensity vs. wavelength characteristic over a wavelength spectrum can be optionally further characterized by a selection from the group consisting of:

a1. a. a third beam from said source of electromagnetic radiation; and b. a second electromagnetic beam combining means;

said second electromagnetic beam combining means being positioned with respect to said commingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means, said second electromagnetic beam combining means being also positioned with respect to said third beam of polychromatic electromagnetic radiation provided by said first Xenon source such that a beam of electromagnetic radiation from said third beam of polychromatic electromagnetic radiation reflects from said second electromagnetic beam combining means such that a second resultant beam of polychromatic electromagnetic radiation which is substantially an output beam of polychromatic electromagnetic radiation which has a relatively even more 193 nm intensity comprising said commingled composite of a plurality of input beams of polychromatic electromagnetic radiation of said first, second and third beams, which first source; and a3. there being present in the pathway of at least one of said beams from said at least one Xenon source a filter which attenuates the intensity of wavelengths other than at 193 nm.

Optionally, or in addition to the foregoing, said material system investigation system can further comprise a back-reflector having a reflective surface;

said back-reflector being situated with respect to said first Xenon source of electromagnetic radiation such that at least some electromagnetic radiation emitted in a direction other than that of the beam of electromagnetic radiation, is redirected into the direction of said beam of electromagnetic radiation thereby; said system being optionally characterized in that said back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

Also optionally or in addition to the foregoing, said material system investigation system can further comprise at least one reflective means in the path of said beam between said source and detector, said at least one reflective means serving to increase the relative intensity of 193 nm electromagnetic radiation at caused to impinge thereupon, as compared to the intensity at visible wavelengths.

Also optionally or in addition to the foregoing, said material system investigation system can comprise a Xenon arc-lamp which presents with an elongated dimension, said Xenon arc-lamp being oriented such that its elongated dimension projects substantially horizontally. Said system can then further comprise means for implementing a selection from the group consisting of:

controlling the vertical location of said Xenon source and a reflective means and means for controlling the rotation of said reflective means, such that in use a beam of electromagnetic beam is produced by said arc-lamp and directed out the lower surface thereof onto said reflective means, which reflectively directs it at an angle-of-incidence onto a sample surface; and controlling the vertical location of a reflective means and means for controlling the rotation and vertical location thereof, such that in use a beam of electromagnetic beam is produced by said arc-lamp and directed out the lower surface thereof onto said reflective means, which reflectively directs it at an angle-of-incidence onto a sample surface.

Also optionally or in addition to the foregoing, said material system investigation system can provide a Xenon arc-lamp presenting with an elongated dimension, said Xenon arc-lamp being oriented such that its elongated dimension projects substantially vertically, said system further comprising double mirror arrangement which rotates the image of said vertically oriented Xenon arc-lamp into a horizontally oriented plane.

More particularly the present invention comprises an ellipsometer system comprising a source of electromagnetic radiation, a polarizer, a stage for supporting a sample, an analyzer and a detector, there optionally being at least one compensator present between said polarizer and stage and/or between said stage and analyzer;

such than in use a beam of electromagnetism is caused to be directed by said source thereof toward a sample placed on said stage, interact with said sample, pass through said analyzer and enter said detector, said beam also passing through any present compensator;

said ellipsometer system being characterized by at least one selection from the group consisting of:

said source of a polychromatic beam of electromagnetic radiation comprises:

a. at least a first Xenon source of polychromatic electromagnetic radiation; and b. at least a first electromagnetic beam combining means;

said at least a first electromagnetic beam combining means being positioned with respect to said first Xenon source of polychromatic electromagnetic radiation such that a beam of polychromatic electromagnetic radiation from said first Xenon source of polychromatic electromagnetic radiation passes through said at least a first electromagnetic beam combining means, and such that another beam of polychromatic electromagnetic radiation from said first Xenon source of polychromatic electromagnetic radiation reflects from said at least a first electromagnetic beam combining means and is commingled with said beam of polychromatic electromagnetic radiation from said first Xenon source of polychromatic electromagnetic radiation which passes through said at least a first electromagnetic beam combining means, said resultant beam of polychromatic electromagnetic radiation substantially being said output beam of polychromatic electromagnetic radiation which has an increased 193 nm intensity;

said source of electromagnetic radiation comprises a back-reflector having a reflective surface, said back-reflector being situated in said source of electromagnetic radiation such that at least some electromagnetic radiation emitted in a direction other than that of the beam of electromagnetic radiation, is redirected into the direction of said beam of electromagnetic radiation thereby; said back-reflector being in a container which has provision for allowing electromagnetic radiation to enter and be reflected back out thereof by said back-reflector, and optionally provision for flowing gas into and out thereof, the purpose of said gas flow being to prevent deposition of contaminants onto said back-reflector reflective surface;

said ellipsometer system further comprises at least one reflective means in the path of said beam between said source and detector, said at least one reflective means serving to increase the relative intensity of 193 nm electromagnetic radiation at caused to impinge thereupon, as compared to the intensity at visible wavelengths;

said Xenon arc-lamp presents with an elongated dimension, said Xenon arc-lamp being oriented such that its elongated dimension projects substantially horizontally, said system further comprising means for controlling the vertical location thereof, said system further comprising a reflective means and means for controlling the vertical location thereof and for rotating said reflective means, such that in use a beam of electromagnetic beam is produced by said arc-lamp and directed out the lower surface thereof onto said reflective means, which reflectively directs it at a first angle-of-incidence onto a sample surface; and said Xenon arc-lamp presents with an elongated dimension, said Xenon arc-lamp being oriented such that its elongated dimension projects substantially horizontally and such that said beam produced by said arc-lamp and directed out the lower surface thereof onto said reflective means, said system providing means for controlling the vertical location of said reflective means and means for controlling the rotation thereof, such that in use a beam of electromagnetic beam is produced by said arc-lamp and directed out the lower surface thereof onto said reflective means, which reflectively directs it at an angle-of-incidence onto a sample surface; and said Xenon arc-lamp presents with an elongated dimension, said Xenon arc-lamp being oriented such that its elongated dimension projects substantially vertically, said system further comprising double mirror arrangement which rotates the image of said vertically oriented Xenon arc-lamp into a horizontally oriented plane.

Said ellipsometer system can comprise a back-reflector comprising:
 an off-axis parabolic mirror; and
 a flat reflecting means;

said off-axis parabolic mirror being positioned to receive electromagnetic radiation from said source, and being positioned substantially in a "backward" projection direction 180 degrees rotated from said "forward" direction, and said flat reflecting means being positioned to receive electromagnetic radiation which reflects from said off-axis parabolic mirror and via reflection direct it directly back to said off-axis parabolic mirror, which off-axis parabolic mirror then directs it back through said source of electromagnetic radiation and along said "forward" direction;

the effect being increased intensity in said "forward" directed beam. Said flat reflecting means can uniformly reflect all wavelengths or said flat reflecting means can reflect different wavelengths with different efficiencies. Further, said flat can reflect IR and/or UV wavelengths more efficiently than visual range wavelengths. Said flat reflecting means can comprise semiconductor, which can be silicon. Said flat reflecting means can comprise silicon with a thin film of other material on its reflective surface which can be SiO2.

Said ellipsometer system can comprise a back-reflector comprising:
 a flat reflecting means; and
 a spherical mirror;

said flat reflecting means being positioned to receive electromagnetic radiation from said source, and being positioned substantially in a "backward" projection direction 180 degrees rotated from said "forward" direction, and said spherical mirror being positioned to receive electromagnetic radiation which reflects from said flat reflecting means and via reflection direct it directly back to said flat reflecting means, which flat reflecting means then directs it back through said source of electromagnetic radiation and along said "forward" direction;

the effect being increased intensity in said "forward" directed beam. Said flat reflecting means can uniformly reflect all wavelengths or said flat reflecting means can reflect different wavelengths with different efficiencies. Further, said flat can reflect IR and/or UV wavelengths more efficiently than visual range wavelengths. Said flat reflecting means can comprise semiconductor, which can be silicon. said flat reflecting means can comprise silicon with a thin film of other material on its reflective surface which can be SiO2.

The present invention will be better understood by reference to the Detailed Description Section of this Disclosure in conjunction with the Drawings.

DETAILED DESCRIPTION

Figure 1A:
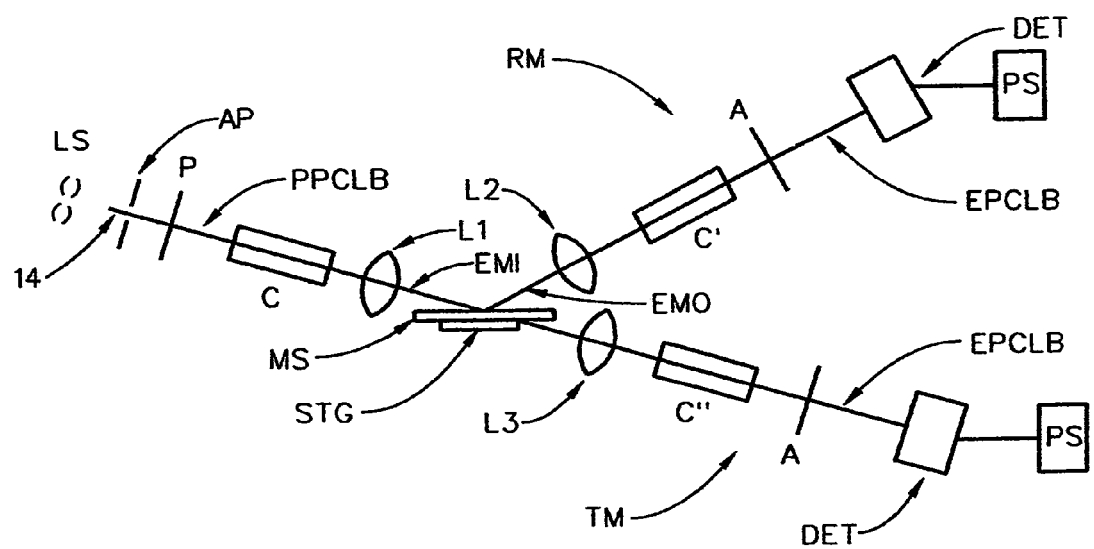
FIG. 1a shows the basic components of Reflectance and Transmission Mode Material System Investigation Systems.
Figure 1B:
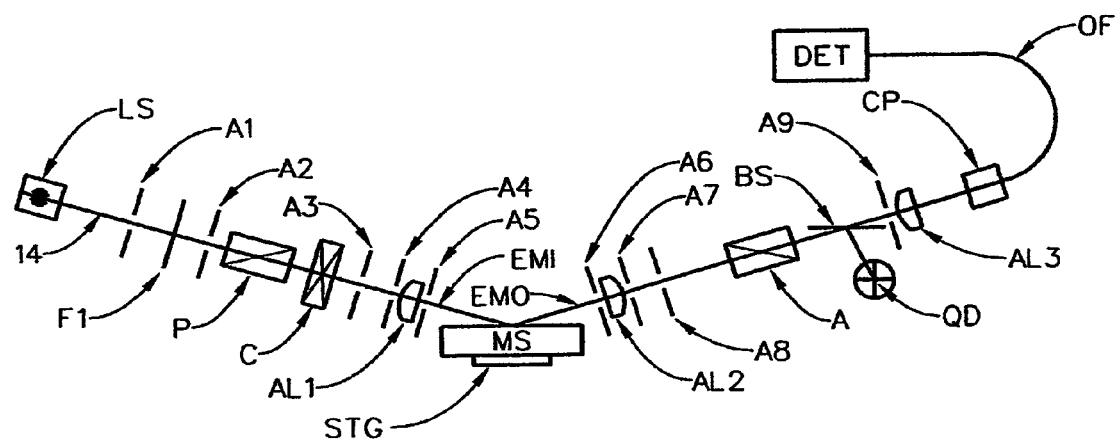
FIG. 1b shows the components of a Reflectance Mode Material System Investigation Systems which has five apertures in the pathway of an electromagnetic beam prior to a material system, and four thereafter.

Presented directly are exemplary systems to which the present invention can be applied in FIGS. 1a and 1b, as well as various systems for altering intensity vs. wavelength characteristics of source of electromagnetic radiation in FIGS. 2a-6b.

Turning now to FIG. 1a, there is shown a demonstrative, non-limiting, ellipsometer system which can be applied to practicing the disclosed invention. There is demonstrated a Material System Investigation System, (ie. a Spectroscopic Ellipsometer System), with provision to investigate a Material System (MS) in either a Reflection Mode (RM) or a Transmission Mode (TM). It is to be noted that said Material System investigation System is generally comprised of a Source (LS) of a Polychromatic Beam (14) of Electromagnetic Radiation, (ie. a Broadband electromagnetic radiation source), a Polarizer Means (P), a Material System, supporting Stage (STG), an Analyzer Means (A) and a Detector Elements (DE's) containing Photo Array Detector Means System (DET). Also note, however, that FIG. 1a shows Reflection Mode System Compensator(s) Means (C) and (C') and Transmission Mode System Compensator(s) Means (C) and (C") as present. It is to be understood that a Compensator Means can be placed ahead of, and/or after a Material System (MS) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 1a also shows the presence of a Processor (PS) for performing calculations that evaluate a sample based on the Detector (DET) intensity output signal. Also indicated are optional Apertures (AP), and Lenses (L1), (L2) and (L3).

It should be appreciated that the configuration in FIG. 1a could be operated as a Rotating Polarizer or Rotating Analyzer System. The disclosed Rotating Compensator Material System Investigation System, however, in the preferred operational mode, essentially fixes the Polarizer Means (P) and Analyzer Means (A) during Data Acquisition from a Material System (Sample) (MS) which is placed upon the Material System supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Material System placed upon said Material System (MS) supporting Stage (STG), only one, or both said Compensator Means can be caused to Rotate in use. If both Compensator Means are caused to rotate, both can be rotated a the same rotation speed, or different rotation speeds can be utilized. It is noted that the J.A. Woollam CO. Rotating Compensator Ellipsometer uses a "Stepper Motor" to cause Compensator rotation, and a common signal synchronizes both the Compensator and Detector. An alternative technique is to use a signal derived from the motor to synchronize the detector means. It is further noted that fixing the Polarizer Means (P) and Analyzer Means (A) in use provides another benefit in that polarization state sensitivity to input and output optics during data acquisition is essentially non-existent. This allows use of Optic Fibers, Mirrors, Beam Splitters, Lenses etc. for input/output.

For insight, FIG. 1b is included to show a preferred polychromatic rotating compensator material system investigation system comprising a source (LS) of polychromatic beam (14) of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector means (DET) which contains a dispersive element and a multiplicity of detector means elements, there further being a UV filter (F1) present between said source (LS) of polychromatic beam of electromagnetic radiation and said stage (STG) for supporting a material system. When said polychromatic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic lens (AL3), enter said optical fiber (OF) and therevia enter said detector means (DET).

As the present invention can be applied to reflectometers and spectrophotometers as well as to ellipsometers and polarimeters, it is noted that removal of polarization state setting, modifying or detecting elements in FIGS. 1a and 1b, (eg. polarizer (P), compensator (C) analyzer (A)), results in a reflectometer or spectrophotometer, where the later term implies reflection or transmission detection capability.

It is also mentioned that in the following it will be generally assumed that a Material System (MS) under investigation by a Spectroscopic Rotating Compensator Material System Investigation System is positioned upon the Material System Supporting Stage (STG). This need not be the case, as is described in U.S. Pat. No. 5,706,087 wherein a Material System (Sample), (MS) can be positioned in a Magneto-Optic System which is physically too large to be supported by said Material System Supporting Stage (STG), or in an environmental control chamber. Further, especially where Ultraviolet range wavelengths are utilized, the system of FIG. 1a or 1b can be placed into an evacuated or purged, (eg. by nitrogen or argon), Chamber to the end that UV absorbing Oxygen and Water Vapor are not present therewithin. The entire FIG. 1a or 1b system can be so encompassed within a said Chamber, or only the Sample (MS) Stage portion thereof. The Chamber, where utilized, can be of multiple region construction.

Again, FIGS. 1a and 1b are included as demonstrative systems which can be applied to practice of the disclosed invention. The method of the disclosed invention involves obtaining data using such systems as a function of an independent variable, (eg. energy or wavelength), and mathematically fitting the data such that a plot of said mathematical function(s) is positioned substantially centrally in said data over a range of said independent variable. The preferred approach to evaluating parameters in the mathematical function is regression, (eg. least square).

Figure 2A:
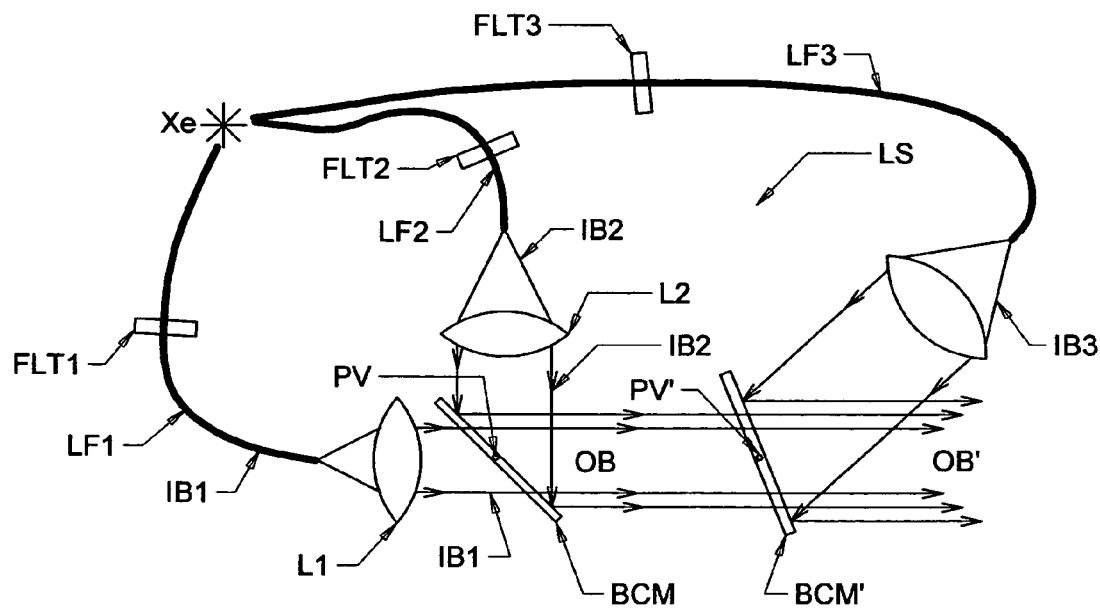
FIG. 2a shows a present invention system for providing an output beam (OB) or (OB') of polychromatic electromagnetic radiation which has a relatively broad and flattened intensity vs. wavelength characteristic over a wavelength spectrum.

Turning now to FIG. 2a, it is shown that the present invention system for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a commingled composite of a plurality of input beams, ((IB1) and (IB2)), of polychromatic electromagnetic radiation which individually do not provide as relatively broad and flattened an intensity vs. wavelength characteristic over said wavelength spectrum, as does said output commingled composite beam of polychromatic electromagnetic radiation, comprises:

a. at least a first (Xe) source of polychromatic electromagnetic radiation; and b. at least one electromagnetic beam combining (BCM) means.

The at least one electromagnetic beam combining means (BCM) is positioned with respect to beams from said at least a first (Xe) source of polychromatic electromagnetic radiation, ((IB1) and (IB2) respectively), such that a beam of polychromatic electromagnetic radiation (IB1) from said (Xe) source of polychromatic electromagnetic radiation passes through said at least one electromagnetic beam combining means (BCM), and such that a beam of polychromatic electromagnetic radiation (IB2), also from said Xe source of polychromatic electromagnetic radiation, reflects from said at least one electromagnetic beam combining means (BCM) and is commingled with said beam of polychromatic electromagnetic radiation (IB1) from said first source (Xe) of polychromatic electromagnetic radiation which passes through said at least one electromagnetic beam combining means (BCM), along a common locus. The resultant beam of polychromatic electromagnetic radiation (OB) is substantially an output beam of polychromatic electromagnetic radiation which has a relatively broad and flattened intensity vs. wavelength over a wavelength spectrum, (as compared to that of the Xenon Source (Xe)), and comprises said commingled composite of a plurality of input beams of polychromatic electromagnetic radiation which individually do not individually provide such a relatively broad and flattened intensity vs. wavelength over a wavelength spectrum characteristic. Also shown in FIG. 2a are collimating lenses (L1) and (L2) to provide collimated beams of electromagnetic radiation ((IB1) and (IB2) respectively), to the electromagnetic beam combining means (BCM), from Xe source of polychromatic electromagnetic radiation.

Further shown in FIG. 2a is an optional third beam of polychromatic electromagnetic radiation (IB3) and a second electromagnetic beam combining means (BCM'). Said second electromagnetic beam combining means (BCM') is positioned with respect to said commingled beam of polychromatic electromagnetic radiation (OB), (which has a relatively broad and flattened intensity vs. wavelength over a wavelength spectrum, comprising wavelengths from source (Xe), which exits said at least a first electromagnetic beam combining means (BCM)) such that said commingled beam of polychromatic electromagnetic radiation (OB) passes through said second electromagnetic beam combining means (BCM). Said second electromagnetic beam combining means (BCM) is further positioned with respect to a third beam from said source (Xe) of polychromatic electromagnetic radiation such that said third beam (IB3) of electromagnetic radiation reflects from said second electromagnetic beam combining means (BCM) to form a second resultant beam of polychromatic electromagnetic radiation (OB') which is substantially an output beam of polychromatic electromagnetic radiation having an even more relatively broadened and flattened intensity vs. wavelength over a wavelength spectrum comprising said commingled composite of a plurality of input beams of polychromatic electromagnetic radiation, (ie. beams (IB1), (IB2) and (IB3)) projected along a common locus. It is emphasized that the source (Xe) individually does not provide such an even more relatively broadened and flattened intensity vs. wavelength over a wavelength spectrum characteristic and thereby is demonstrated the utility of the present invention.

Note the indication of the presence of Filters (FLT1) (FLT2) and (FLT3) in the system of FIG. 2a which can optionally be used to attenuate the intensity of other than 193 nm wavelengths.

A system as shown in FIG. 2a preferably include a pivot(s) (PV) (PV') to allow the beam combining means (BCM) and/or (BCM'), respectively, to be rotated. A direct application of the use of pivot(s) (PV), particularly where two degrees of rotational freedom are allowed thereby, is to allow making beam combining means transmitted and reflected electromagnetic beam components coincident in output beams (OB) and (OB'). Where electromagnetic beams (IB2) and (IB3) can be moved, pivot(s) (PV) can also be beneficially applied to allow selection of an optimum angle at which a beam of electromagnetic radiation is caused to reflect from a beam combining means in use. The reason this might be desirable is that the angle at which a beam of electromagnetic radiation approaches a beam combining means affects the percent of an impinging beam which actually reflects therefrom and becomes part of the output beam (OB).

Figure 2B:
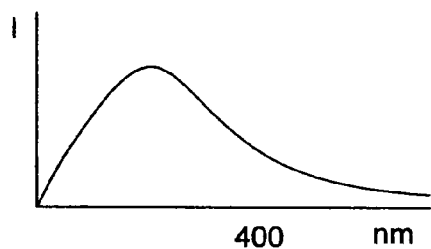
FIG. 2b demonstrates a spectrum of a polychromatic electromagnetic radiation (IB1) from a source (Xe) of polychromatic electromagnetic radiation which passes through said at least one electromagnetic beam combining means (BCM).
Figure 2C:
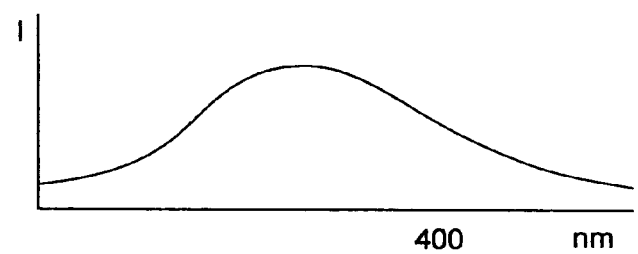
FIG. 2c demonstrates a beam of polychromatic electromagnetic radiation (IB2) from said source (Xe) of polychromatic electromagnetic radiation exits said at least one electromagnetic beam combining means (BCM).
Figure 2D:
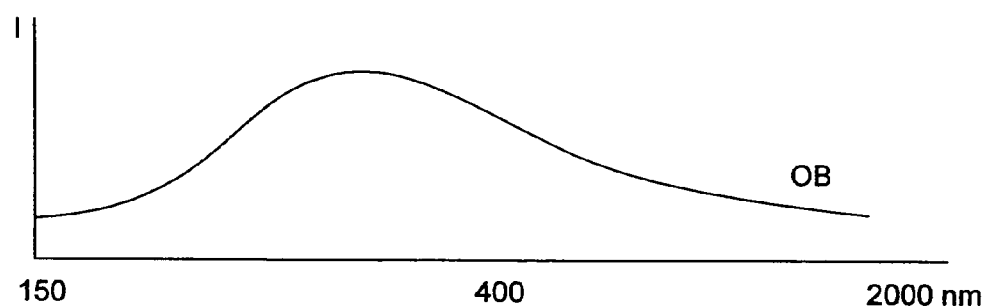
FIG. 2d demonstrates a resultant beam of polychromatic electromagnetic radiation (OB) which is substantially a commingled composite of a plurality of input beams (IB1) and (IB2) of polychromatic electromagnetic radiation which individually do not provide such a relatively broad and flattened intensity vs. wavelength over a wavelength spectrum characteristic as demonstrated in FIGS. 2b and 2c.

FIG. 2b demonstrates a spectrum of a polychromatic electromagnetic radiation (IB1) from said first source (Xe) of polychromatic electromagnetic radiation which passes through said at least one electromagnetic beam combining means (BCM). FIG. 2c demonstrates a combination of polychromatic electromagnetic radiation beams (IB1) and (IB2) from said at least one electromagnetic beam combining means (BCM). FIG. 2d demonstrates a resultant beam of polychromatic electromagnetic radiation (OB') which is substantially a commingled composite of a plurality of input beams (IB1), (IB2) and (IB3) of polychromatic electromagnetic radiation which individually do not provide such a relatively broad and flattened intensity vs. wavelength over a wavelength spectrum characteristic as demonstrated in FIGS. 2b and 2c. It is to be understood that the graphs in FIGS. 2c and 2d are demonstrative only, and it is noted use of appropriate Filters (FLT1) (FLT2) and (FLT3) could more greatly favor 193 nm intensity over that at other wavelengths than is shown therein. As the present invention is spectroscopic, however, a complete attenuation of intensity at other than 193 nm is not desired. What is desired is a more flat intensity vs. wavelength spectrum from a Xenon arc-lamp than is provided thereby directly. It is also mentioned at this point that detector gain can be set higher without saturating the electronics therein when the intensity of Visible wavelengths from a Xenon arc-lamp are attenuated. This enables better detection of the intensity at IR and UV, (eg. 193 nm), wavelengths.

Figure 3A:
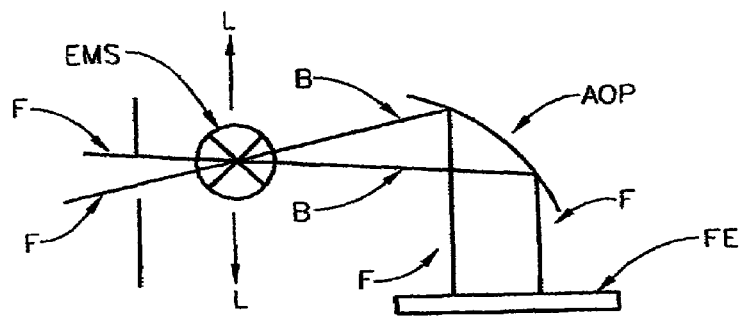
FIG. 3a shows a back-reflector system comprising an off-axis parabolic (OAP) back-reflector to a flat reflector.
Figure 3B:
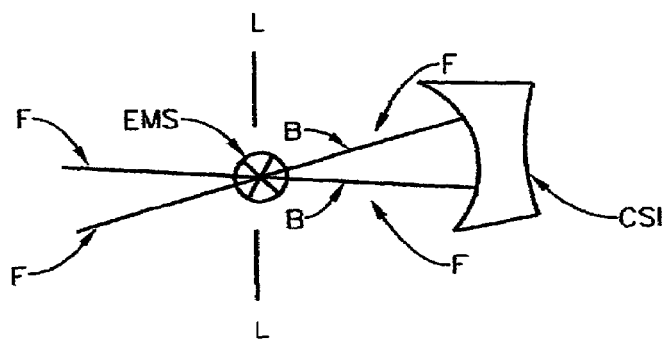
FIG. 3b demonstrates a concave back reflector (CSI).
Figure 3C:
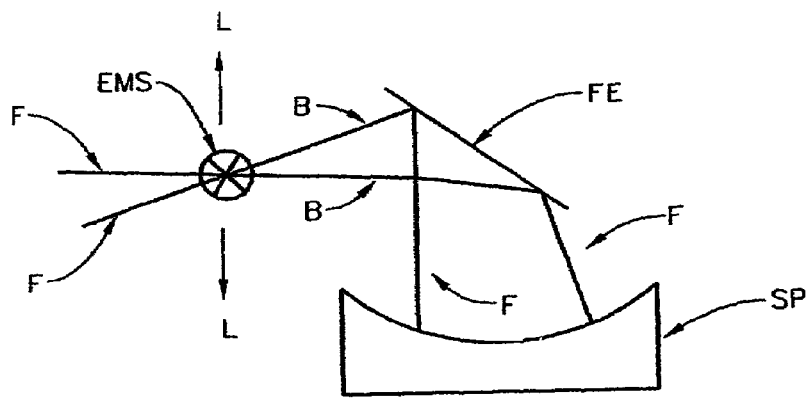
FIG. 3c shows a back-reflector comprising a flat mirror (FE) and a spherical mirror (SP).

The disclosed invention can also utilize reflecting means for application in redirecting backside electromagnetic radiation emitted by a source (EMS), (eg. a Xenon arc-lamp), thereof. FIG. 3a shows a Source (EMS) of electromagnetic radiation and a first reflecting means comprised of an Off-Axis Parabolic Mirror (OAP) and a Flat Reflecting Element (FE), in that sequential order. FIG. 3b shows a Source (EMS) of electromagnetic radiation, and a second reflecting means comprising a Concave Si Mirror (CSI), which can have a thin film of Oxide or other material thereupon, to effect different reflection efficiencies at different wavelengths. FIG. 3c shows a Source (EMS) of electromagnetic radiation and third reflecting means comprising a Flat Reflecting Element (FE) and a spherical mirror (SP), in that sequential order.

In all three cited examples, note that electromagnetic radiation emits from the Source thereof (EMS) in a "Forward" (F) direction, and in a "Backward" (B) direction. Note The radiation emitted in the "Backward" direction (B) is, in each of the FIGS. 3a, 3b and 3c examples redirected toward the "Forward" (F) direction. Radiation identified as (L) is lost, but could, for instance, be focused onto a light fiber and directed for application in sample alignment.

It is also mentioned that some or all of the reflecting means can be affixed to adjustment means to enable directing an electromagnetic beam in an optimum manner.

It should be appreciated that the Material, (eg. Silicon, possibly with a thin layer of Oxide or other materials thereupon), serves to reflect different wavelengths with different efficiency. For instance, Si with a 600 A film of SiO2 has been found to reflect UV and IR wavelengths more efficiently than Visible Wavelengths. This leads to a more uniform Intensity vs. Wavelength Spectrum in the beam directed in the "Forward" direction.

Figure 3D:
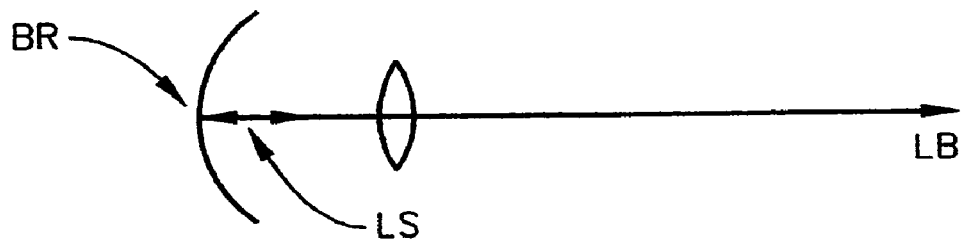
FIG. 3d shows a Source (LS) of Electromagnetic Radiation, and a Back-Reflector (BR) positioned to redirect electromagnetic radiation emitted opposite to the direction of a Beam (LB) thereof, into the direction of a beam (LB) thereof.
Figure 3E:
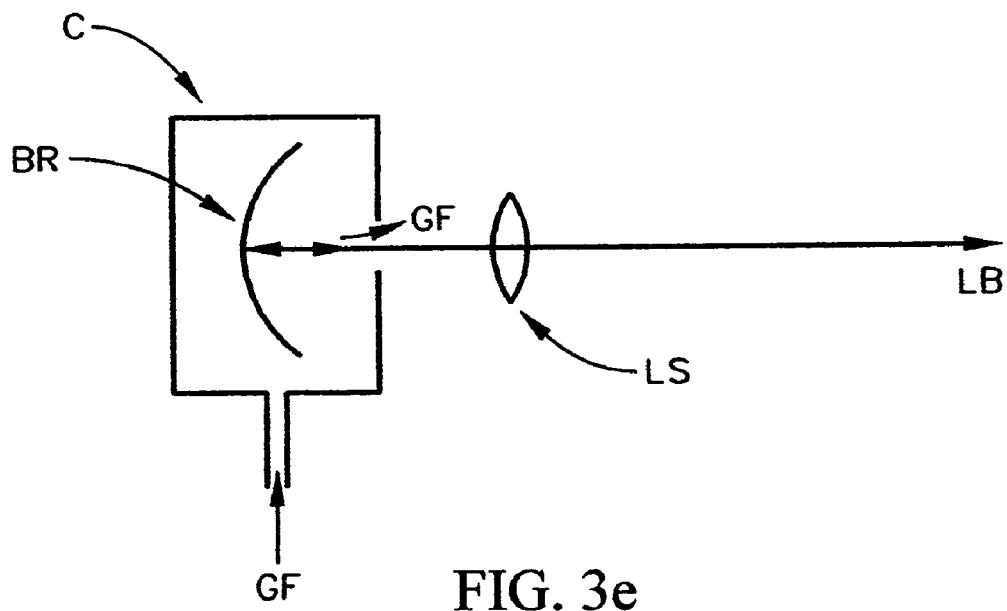
FIG. 3e shows the Back-Reflector (BR) of FIG. 1 in a Container (C) which allows for the flow of Gas (GF) into and out thereof.
Figure 3F:
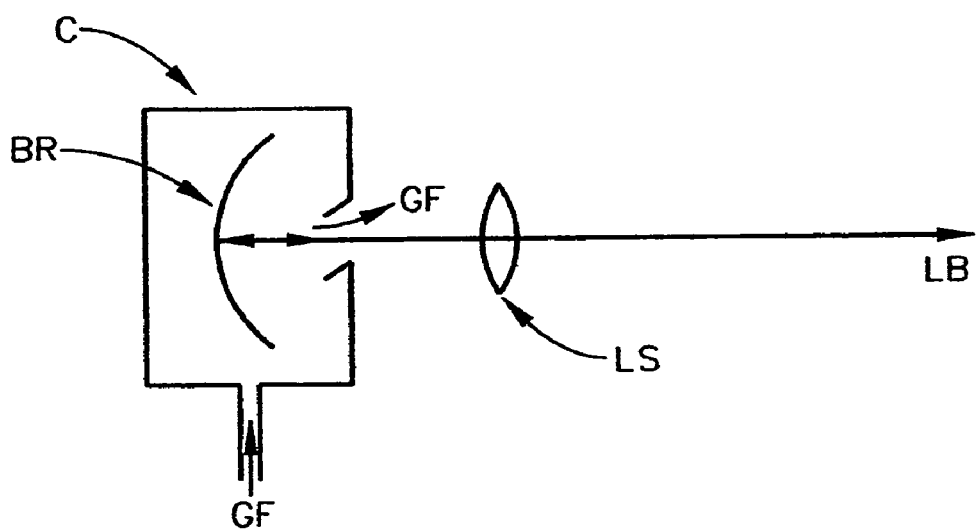
FIG. 3f is a variation of FIG. 6a, and shows that the Gas Flow (GF) out of the Container (C) can be directed away from the Source (LS) of Electromagnetic Radiation.

Turning now to FIG. 3d, there is shown a Source (LS) of Electromagnetic Radiation, and a Back-Reflector (BR) positioned to redirect electromagnetic radiation emitted opposite to the direction of a Beam (LB) thereof, into the direction of a beam (LB) thereof. FIG. 3e shows the Back-Reflector (BR) of FIG. 3d in a Box (B) which allows for the flow of Gas (GF) into and out thereof. FIG. 3f is a variation of FIG. 3e, wherein the Gas Flow (GF) out of the Container (C) is directed away from the Source (LS) of Electromagnetic Radiation. This has been found beneficial because it avoids detrimental cooling of the Source (S).

Figure 4A:
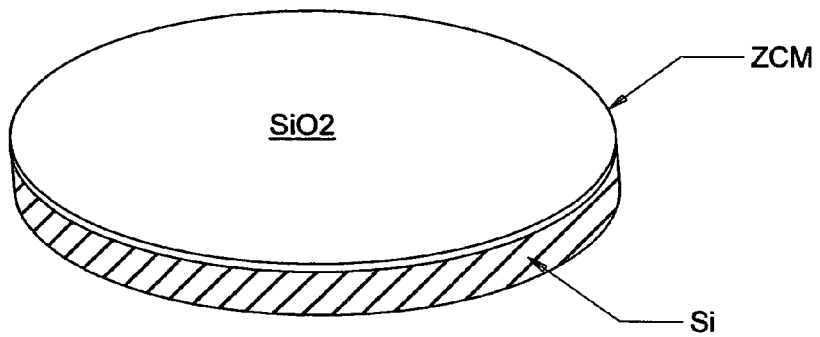
FIG. 4a shows a Silicon Wafer with Silicon Dioxide (SiO$_2$) on the surface thereof, as a composite identified as (ZCM).
Figure 4B:
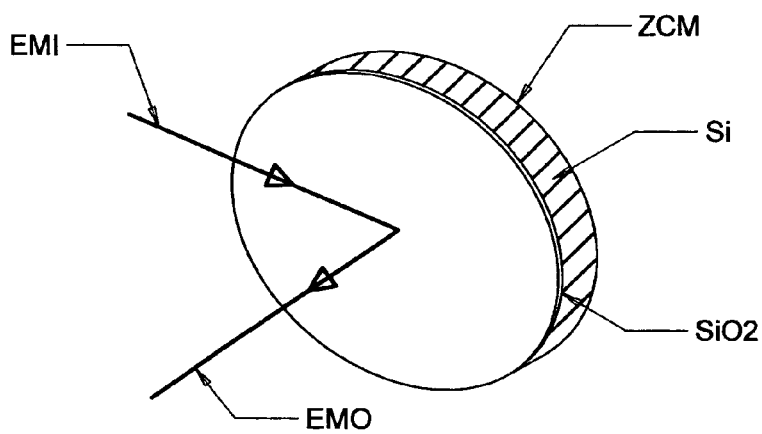
FIG. 4b shows Incident (EMI) and Reflected (EMO) electromagnetic radiation.
Figure 4F:
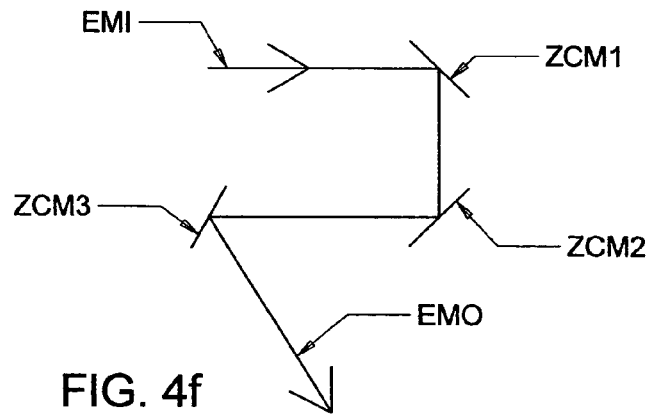
FIG. 4f demonstrates that a beam (EMI) can be caused to undergo multiple reflections from a FIG. 4a system.
Figure 4C:
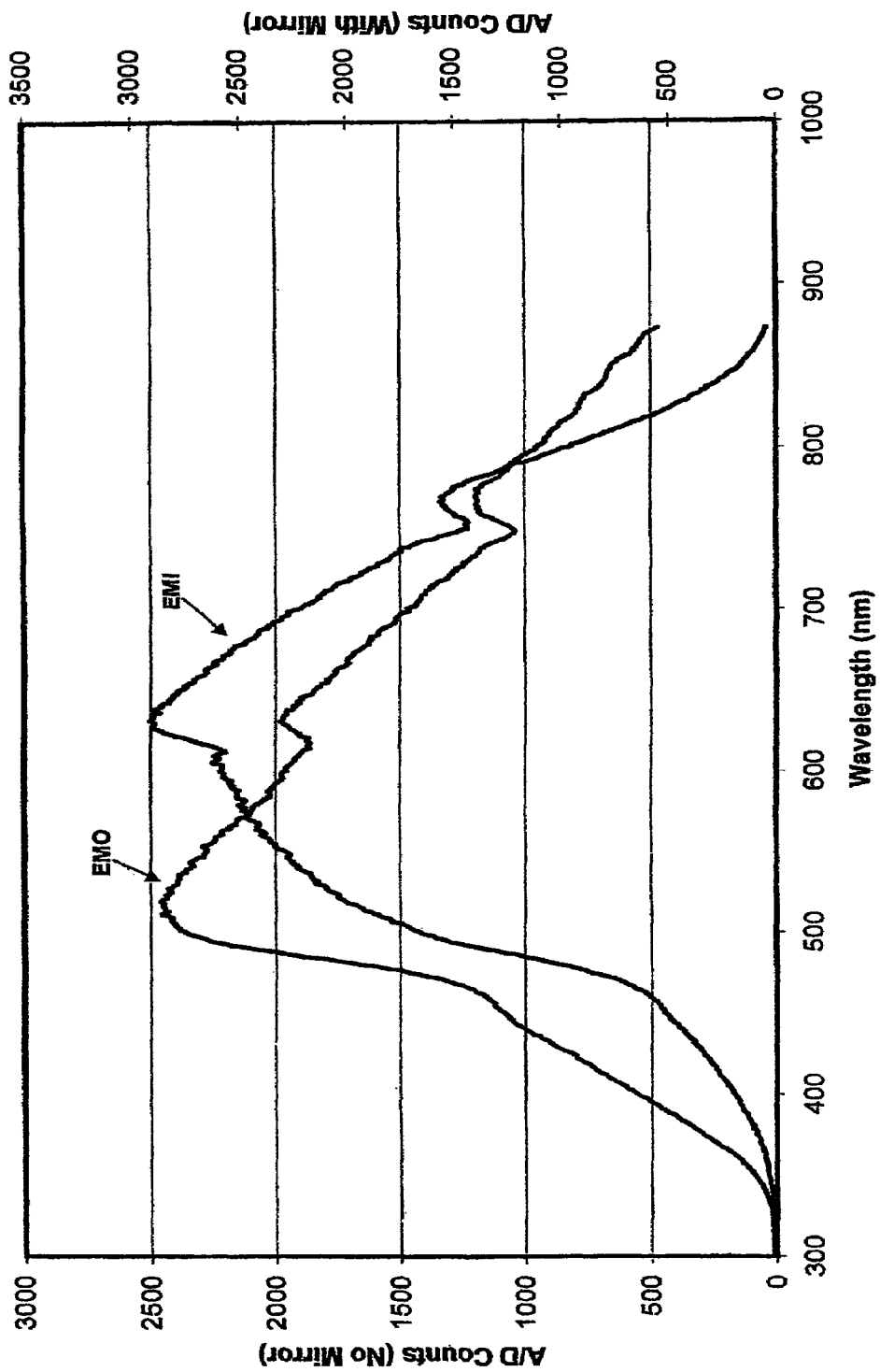
FIG. 4c shows how the relative intensities of (EMI) and (EMO) are changed by the FIG. 4b interaction with (ZCM).
Figure 4E:
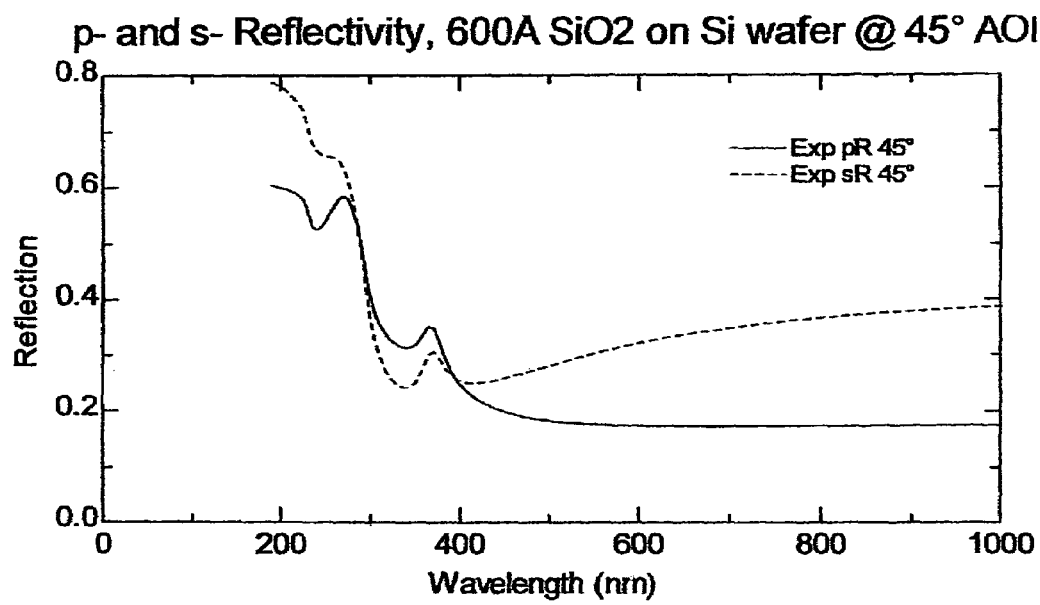
FIGS. 4d and 4e demonstrate the effects of application of two (ZCM) systems to p and s components of a beam (EMI).
Figure 4D:
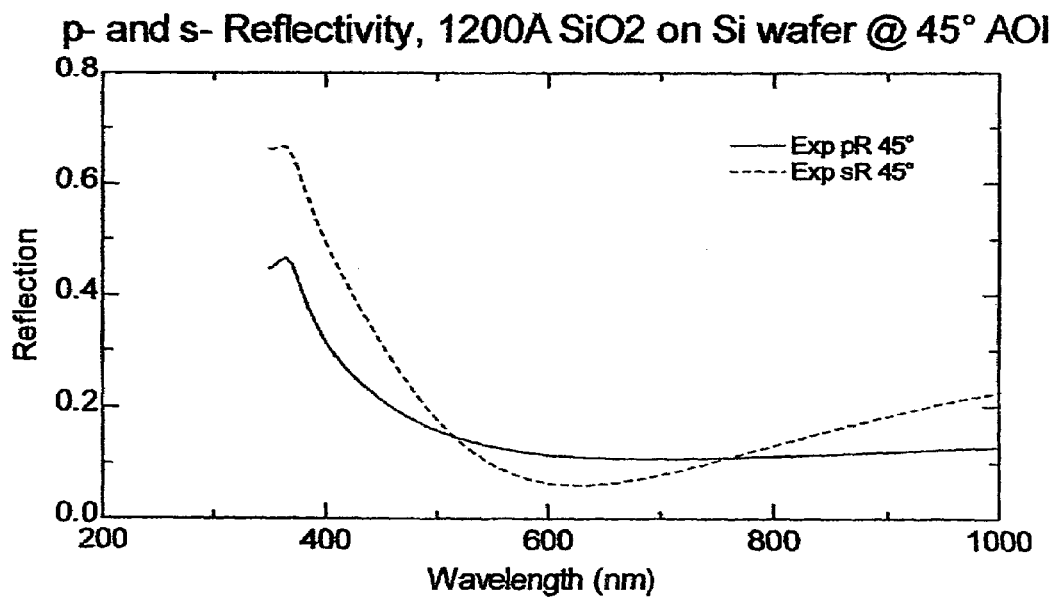

FIGS. 4a, 4b and 4c demonstrate use of a reflecting means to change relative intensities of electromagnetic radiation caused to impinge thereupon. Shown in FIG. 4a is a Silicon Wafer with Silicon Dioxide ($SiO_2$) on the surface thereof, as a composite identified as (ZCM). FIG. 4b shows Incident (EMI) and Reflected (EMO) electromagnetic radiation and FIG. 4c shows how the relative intensities of (EMI) and (EMO) are changed by the FIG. 4b interaction with (ZCM). Note that shorter and longer wavelength intensities are enhanced. FIGS. 4d and 4e demonstrate effects of application of (ZCM) to direct beam (EMI). FIG. 4f demonstrates that a beam (EMI) can be caused to undergo multiple reflections from a FIG. 4a system. When this is done the effects shown in FIG. 4c are compounded so that the effects on UV and IR intensities are multiplied. Further, when Visual wavelength intensities are decreased the Xenon Source wattage can be increased so that intensities at all wavelengths are increased, including those at 193 nm. However, detector circuitry will not be saturated by relatively greater Visual wavelength intensities, as said visual wavelength intensities are attenuated, making them more comparable to the 193 nm intensity.

Figure 5A:
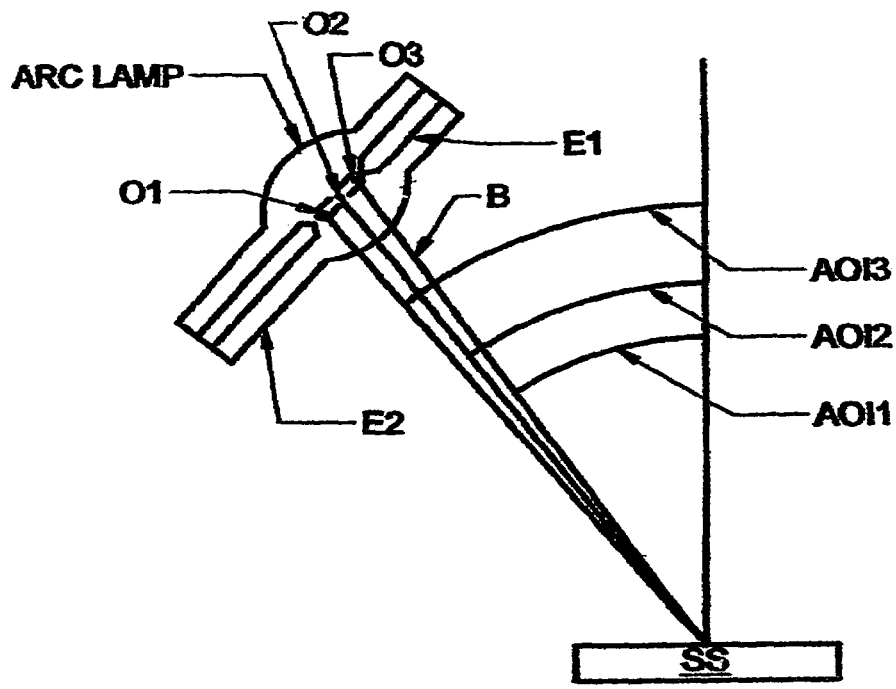
FIG. 5a shows how a the effective source point (eg. O1, O2, O3), of a substantially vertically oriented arc-lamp can change over time of use, and how that change can affect the angle-of-incidence the Beam (E) from said arc-lamp to the surface of the sample changes in response, (eg. AOI3, AOI2) AOI1).

FIG. 5a shows how a the effective source point (eg. O1, O2, O3), of a substantially vertically oriented arc-lamp can change over time of use, and how that change can affect the angle-of-incidence the Beam (E) from said arc-lamp to the surface of the sample changes in response, (eg. AOI3, AOI2) AOI1).

Figure 5B:
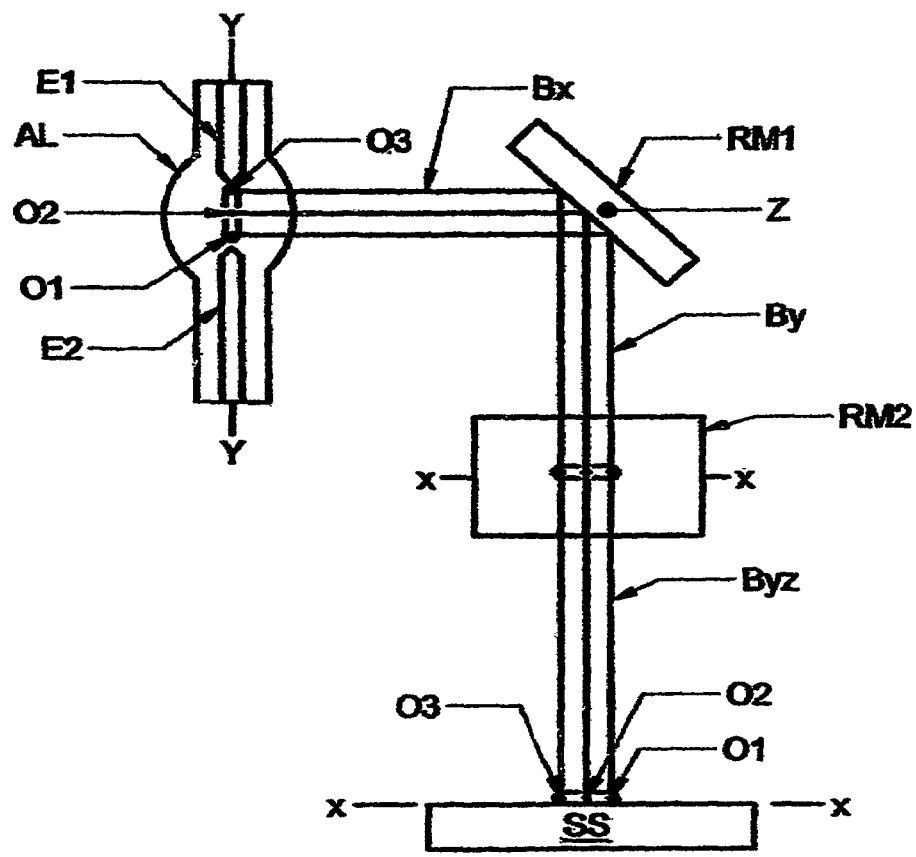
FIGS. 5b and 5c show a system comprising a double mirror (RM1) (RM2) arrangement to rotate the image of a vertically oriented arc-lamp (AL) into a horizontally oriented plane.
Figure 5C:
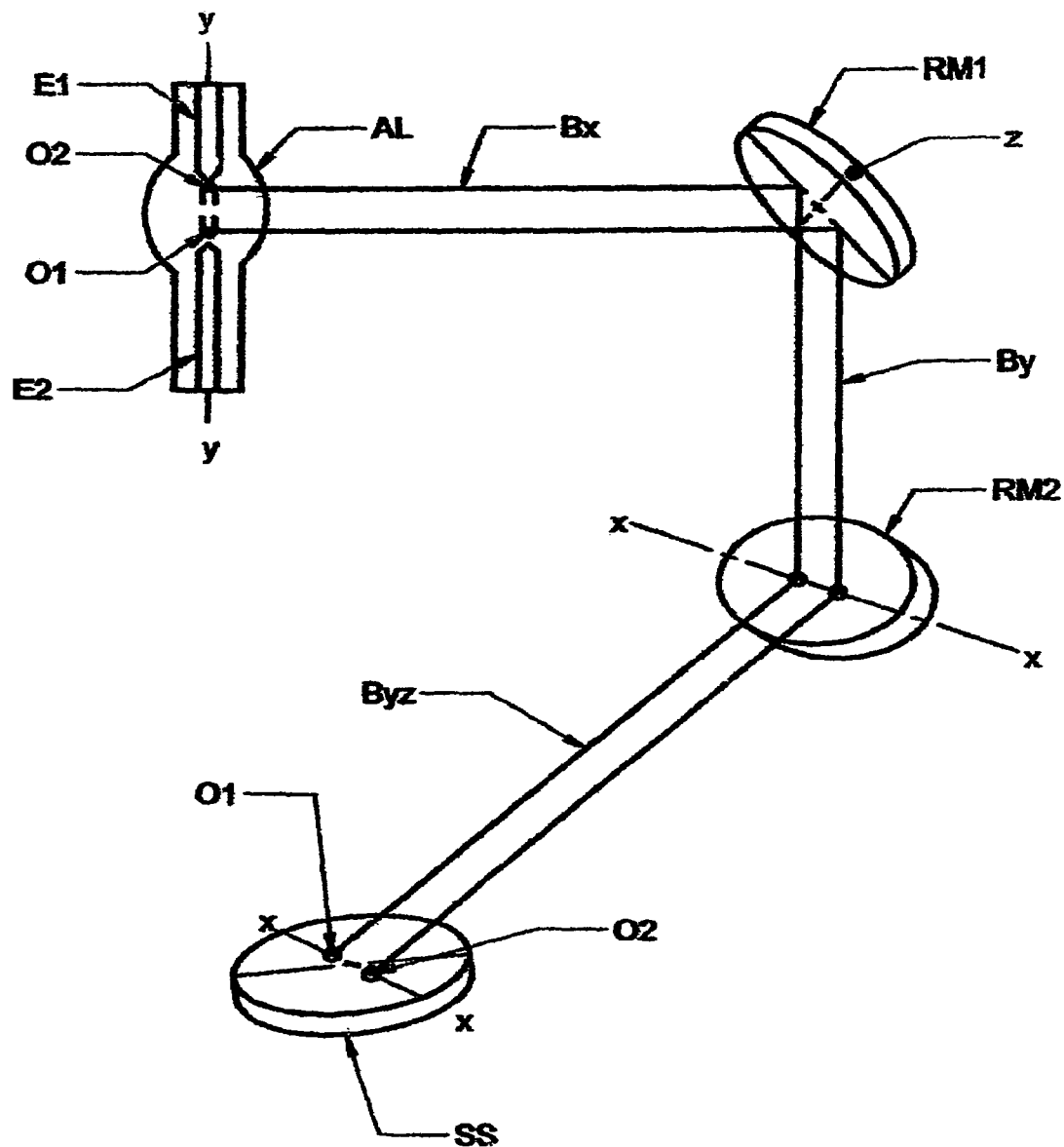

FIGS. 5b and 5c show a system comprising a double mirror (RM1) (RM2) arrangement to rotate the image of a vertically oriented arc-lamp (AL) into a horizontally oriented plane. This is Claimed in patent application Ser. No. 11/084,827.

Figure 6A:
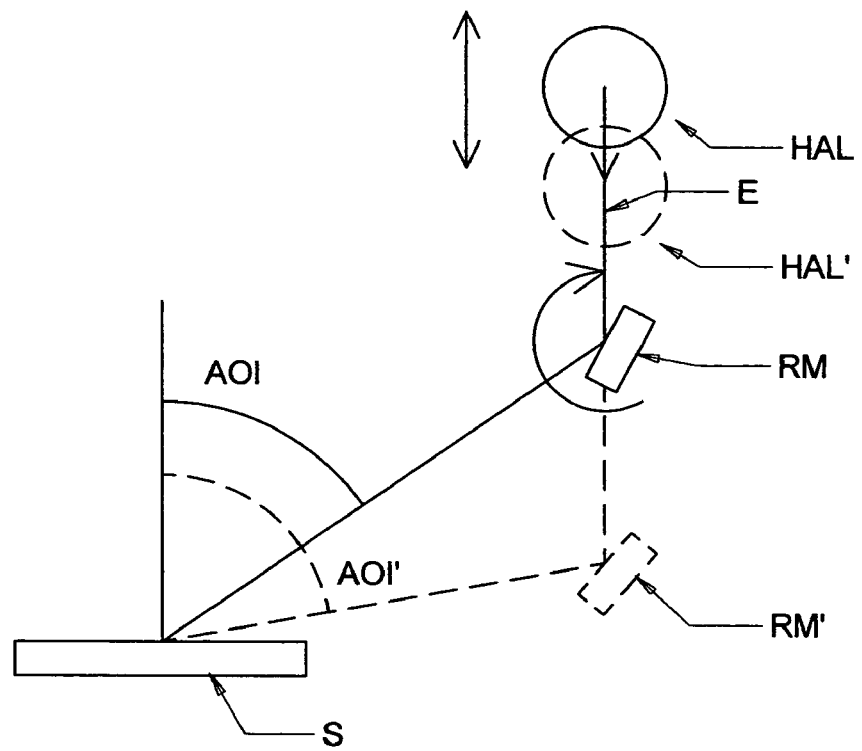
FIGS. 6a and 6b show an approach of using a horizontally oriented arc-lamp (HAL) from which a beam (E) always exists the lower surface thereof and reflects from a reflective means (RM).
Figure 6B:
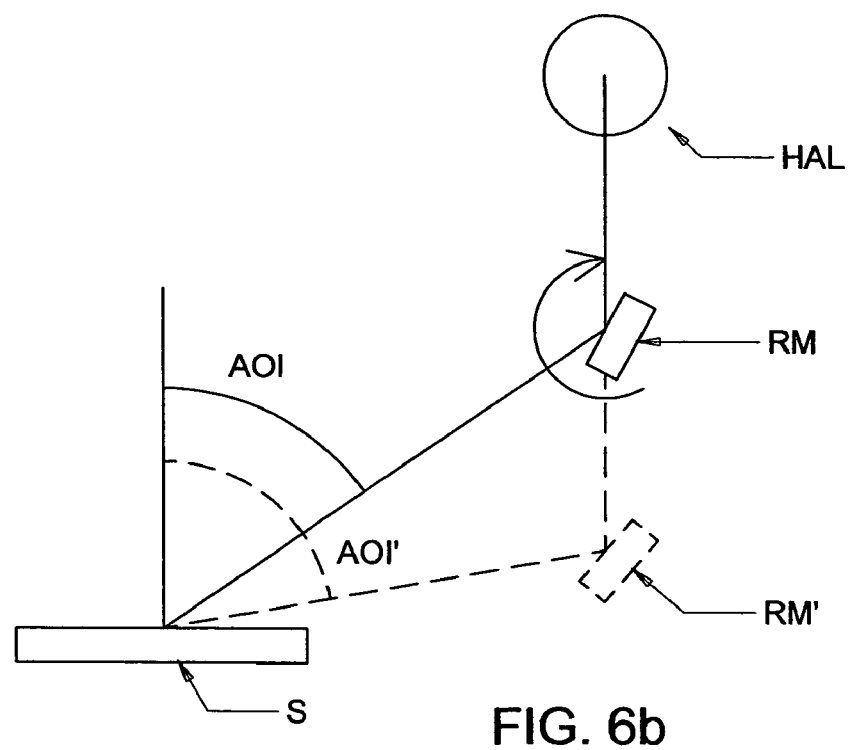

FIG. 6a shows the present invention approach of using a horizontally oriented arc-lamp (HAL) from which a beam (E) always exists the lower surface thereof and reflects from a reflective means (RM). The angle-of-incidence (AOI) of said beam to the sample surface is determined by the angle of said reflective means (RM). Note that if the arc-lamp (HAL') is moved downward and the reflective means (RM') is also moved down and rotated as shown, the angle-of-incidence (AOI) is changed, but that the beam (E) still exits the lower portion of the horizontally oriented arc-lamp. FIG. 6b shows a variation on FIG. 6a, wherein only the reflective means (RM) is moved and rotated to position (RM'), and the arc-lamp (HAL) remains stationary.

FIGS. 2a-6b therefore demonstrate various non-limiting approaches to enhancing the intensity of 193 nm electromagnetic radiation provided by a Xenon arc-lamp, as compared to other wavelengths produced thereby.

Finally, while 193 nm has been used as an example herein as it is an important wavelength in semiconductor fabrication, the present invention is broader in scope and can be used to provide UV and deep UV wavelengths generally. The Claims should be read to interpret the language "UV/deep UV" to include 193 nm.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A material system investigation system comprising at least one Xenon source of a polychromatic beam of electromagnetic radiation, a material system supporting stage, a detector, and a processor for performing calculations that evaluate detector output signal;

there optionally being present a polarizer between said source and said material system supporting stage, an analyzer between said material system supporting stage and said detector, and optionally at least one compensator between said polarizer and analyzer;

such that in use said Xenon source of a polychromatic beam of electromagnetic radiation is caused to provide a beam of electromagnetic radiation and direct it to interact with a sample which is placed on said material system supporting stage after optionally passing through said polarizer and analyzer and at least one compensator, and into said detector which in turn produces data corresponding to a parameter vs. at least one selection from the group consisting of:

angle-of-incidence; and wavelength;

including mathematical equivalents thereof;

said material system investigation system being characterized in that said source of a polychromatic beam of electromagnetic radiation comprises only at least one Xenon arc lamp which is used to provide UV/deep UV wavelength electromagnetic radiation without application of a supplemental source of electromagnetic radiation, in optional combination with a means for attenuating the intensity of other wavelengths.

2. A material system investigation system as in claim 1, in which said source of a polychromatic beam of electromagnetic radiation comprises:
  a. at least a first Xenon source of polychromatic electromagnetic radiation; and
  b. at least a first electromagnetic beam combining means;
said at least a first electromagnetic beam combining means being positioned with respect to said first Xenon source of polychromatic electromagnetic radiation such that a beam of polychromatic electromagnetic radiation from said first Xenon source of polychromatic electromagnetic radiation passes through said at least a first electromagnetic beam combining means, and such that another beam of polychromatic electromagnetic radiation from said first Xenon source of polychromatic electromagnetic radiation reflects from said at least a first electromagnetic beam combining means and is commingled with said beam of polychromatic electromagnetic radiation from said first Xenon source of polychromatic electromagnetic radiation which passes through said at least a first electromagnetic beam combining means, said resultant beam of polychromatic electromagnetic radiation substantially being said output beam of polychromatic electromagnetic radiation which has an increased UV/deep UV intensity; said system for providing an output beam of polychromatic electromagnetic radiation which has a relatively broad and flattened intensity vs. wavelength characteristic over a wavelength spectrum being optionally further characterized by a selection from the group consisting of:
  a1. a. a third beam from said source of electromagnetic radiation; and
  b. a second electromagnetic beam combining means;
    said second electromagnetic beam combining means being positioned with respect to said commingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means, said second electromagnetic beam combining means being also positioned with respect to said third beam of polychromatic electromagnetic radiation provided by said first Xenon source such that a beam of electromagnetic radiation from said third beam of polychromatic electromagnetic radiation reflects from said second electromagnetic beam combining means such that a second resultant beam of polychromatic electromagnetic radiation which is substantially an output beam of polychromatic electromagnetic radiation which has a relatively even more UV/deep UV intensity comprising said commingled composite of a plurality of input beams of polychromatic electromagnetic radiation of said first, second and third beams, which first source; and
  a3. there being present in the pathway of at least one of said beams from said at least one Xenon source a attenuates means for attenuating the intensity of wavelengths other than at UV/deep UV.
3. A material system investigation system as in claim 1, which further comprises a back-reflector having a reflective surface;
  said back-reflector being situated with respect to said at least one Xenon source of electromagnetic radiation such that at least some electromagnetic radiation emitted in a direction other than that of the beam of electromagnetic radiation, is redirected into the direction of said beam of electromagnetic radiation thereby;
  said system being optionally characterized in that said back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.
4. A material system investigation system as in claim 3, in which said Xenon arc-lamp presents with an elongated dimension, said Xenon arc-lamp being oriented such that its elongated dimension projects substantially vertically, said system further comprising double mirror arrangement which rotates the image of said Xenon arc-lamp into a horizontally oriented plane.
5. A material system investigation system as in claim 1, which further comprises at least one reflective means in the path of said beam between said at least one Xenon source and detector, said at least one reflective means serving to increase the relative intensity of UV/deep UV electromagnetic radiation at caused to impinge thereupon, as compared to the intensity at visible wavelengths.
6. A material system investigation system as in claim 1, in which said at least one Xenon arc-lamp presents with an elongated dimension, said Xenon arc-lamp being oriented such that its elongated dimension projects substantially horizontally;
  said system further comprising means for implementing a selection from the group consisting of:
    controlling the vertical location of said Xenon source and a reflective means and means for controlling the rotation of said reflective means, such that in use a beam of electromagnetic beam is produced by said arc-lamp and directed out the lower surface thereof onto said reflective means, which reflectively directs it at an angle-of-incidence onto a sample surface; and
    controlling the vertical location of a reflective means and means for controlling the rotation and vertical location thereof, such that in use a beam of electromagnetic beam is produced by said arc-lamp and directed out the lower surface thereof onto said reflective means, which reflectively directs it at an angle-of-incidence onto a sample surface.
7. A material system investigation system as in claim 1, in which said Xenon arc-lamp presents with an elongated dimension, said Xenon arc-lamp being oriented such that its elongated dimension projects substantially vertically, said system further comprising double mirror arrangement which rotates the image of said Xenon arc-lamp into a horizontally oriented plane.
8. An ellipsometer system comprising a source of electromagnetic radiation, a polarizer, a stage for supporting a sample, an analyzer and a detector, there optionally being at least one compensator present between said polarizer and analyzer;
  such than in use a beam of electromagnetism is caused to be directed by said source thereof toward a sample placed on said stage, interact with said sample, pass through said analyzer and enter said detector, said beam also passing through any present compensator;
  said ellipsometer system being characterized by at least one selection from the group consisting of:
    said source of a polychromatic beam of electromagnetic radiation comprises:
      a. at least a first Xenon source of polychromatic electromagnetic radiation; and
      b. at least a first electromagnetic beam combining means;

with said at least a first electromagnetic beam combining means being positioned with respect to said first Xenon source of polychromatic electromagnetic radiation such that a beam of polychromatic electromagnetic radiation from said first Xenon source of polychromatic electromagnetic radiation passes through said at least a first electromagnetic beam combining means, and such that another beam of polychromatic electromagnetic radiation from said first Xenon source of polychromatic electromagnetic radiation reflects from said at least a first electromagnetic beam combining means and is commingled with said beam of polychromatic electromagnetic radiation from said first Xenon source of polychromatic electromagnetic radiation which passes through said at least a first electromagnetic beam combining means, said resultant beam of polychromatic electromagnetic radiation substantially being said output beam of polychromatic electromagnetic radiation which has an increased UV/deep UV intensity;

said source of electromagnetic radiation comprises a back-reflector having a reflective surface, said back-reflector being situated in said source of electromagnetic radiation such that at least some electromagnetic radiation emitted in a direction other than that of the beam of electromagnetic radiation, is redirected into the direction of said beam of electromagnetic radiation thereby; said back-reflector being in a container which has provision for allowing electromagnetic radiation to enter and be reflected back out thereof by said back-reflector, and optionally provision for flowing gas into and out thereof, the purpose of said gas flow being to prevent deposition of contaminants onto said back-reflector reflective surface;

said ellipsometer system further comprises at least one reflective means in the path of said beam between said source and detector, said at least one reflective means serving to increase the relative intensity of UV/deep UV electromagnetic radiation caused to impinge thereupon, as compared to the intensity at visible wavelengths;

said Xenon arc-lamp presents with an elongated dimension, said Xenon arc-lamp being oriented such that its elongated dimension projects substantially horizontally, said system further comprising means for controlling the vertical location thereof, said system further comprising a reflective means and means for controlling the vertical location thereof and for rotating said reflective means, such that in use a beam of electromagnetic beam is produced by said arc-lamp and directed out the lower surface thereof onto said reflective means, which reflectively directs it at a first angle-of-incidence onto a sample surface; and said Xenon arc-lamp presents with an elongated dimension, said Xenon arc-lamp being oriented such that its elongated dimension projects substantially horizontally and such that said beam produced by said arc-lamp and directed out the lower surface thereof onto said reflective means, said system providing means for controlling the vertical location of said reflective means and means for controlling the rotation thereof, such that in use a beam of electromagnetic beam is produced by said arc-lamp and directed out the lower surface thereof onto said reflective means, which reflectively directs it at an angle-of-incidence onto a sample surface; and said Xenon arc-lamp presents with an elongated dimension, said Xenon arc-lamp being oriented such that its elongated dimension projects substantially vertically, said system further comprising double mirror arrangement which rotates the image of said vertically oriented Xenon arc-lamp into a horizontally oriented plane.

9. An ellipsometer system comprising as in claim 8, which comprises a back-reflector-comprising:
an off-axis parabolic mirror; and
a flat reflecting means;
said off-axis parabolic mirror being positioned to receive electromagnetic radiation from said source, and being positioned substantially in a "backward" projection direction 180 degrees rotated from said "forward" direction, and said flat reflecting means being positioned to receive electromagnetic radiation which reflects from said off-axis parabolic mirror and via reflection direct it directly back to said off-axis parabolic mirror, which off-axis parabolic mirror then directs it back through said source of electromagnetic radiation and along said "forward" direction;
the effect being increased intensity in said "forward" directed beam.

10. A system as in claim 9 in which said flat reflecting means uniformly reflects all wavelengths.

11. A system as in claim 9 in which said flat reflecting means reflects different wavelengths with different efficiencies.

12. A system as in claim 11 in which said flat reflecting means reflects IR and UV wavelengths more efficiently than visual range wavelengths.

13. A system as in claim 9 in which said flat reflecting means comprises semiconductor.

14. A system as in claim 13 in which said flat reflecting means comprises silicon.

15. A system as in claim 14 in which said flat reflecting means comprises silicon with a thin film of other material on its reflective surface.

16. A system as in claim 15 in which said thin film of other material on said reflective surface is SiO2.

17. An ellipsometer system comprising as in claim 8, which comprises a back-reflector comprising:
a flat reflecting means; and
a spherical mirror;
said flat reflecting means being positioned to receive electromagnetic radiation from said source, and being positioned substantially in a "backward" projection direction 180 degrees rotated from said "forward" direction, and said spherical mirror being positioned to receive electromagnetic radiation which reflects from said flat reflecting means and via reflection direct it directly back to said flat reflecting means, which flat reflecting means then directs it back through said source of electromagnetic radiation and along said "forward" direction;
the effect being increased intensity in said "forward" directed beam.

18. A system as in claim 17 in which said flat reflecting means substantially uniformly reflects all wavelengths.

19. A system as in claim 17 in which said flat reflecting means reflects different wavelengths with different efficiencies.

20. A system as in claim 17 in which said flat reflecting means reflects IR and UV wavelengths more efficiently than visual range wavelengths.

21. A system as in claim 17 in which said flat reflecting means comprises semiconductor.

22. A system as in claim 21 in which said flat reflecting means comprises silicon.

23. A system as in claim 17 in which said flat reflecting means comprises silicon with a thin film of other material on its reflective surface.

24. A system as in claim 23 in which said thin film of other material on said reflective surface is SiO2.

25. A system as in claim 8 in which the Xenon lamp operates at less than 500 watts.

26. A material system investigation system comprising at least one Xenon source of a polychromatic beam of electromagnetic radiation, a material system supporting stage, a detector, and a processor for performing calculations that evaluate detector output signal;

there optionally being present a polarizer between said source and said material system supporting stage, an analyzer between said material system supporting stage and said detector, and optionally at least one compensator between said polarizer and analyzer;

such that in use said Xenon source of a polychromatic beam of electromagnetic radiation is caused to provide a beam of electromagnetic radiation and direct it to interact with a sample which is placed on said material system supporting stage after optionally passing through said polarizer and analyzer and at least one compensator, and into said detector which in turn produces data corresponding to a parameter vs. at least one selection from the group consisting of:

angle-of-incidence; and wavelength;

including mathematical equivalents thereof;

said material system investigation system being characterized in that said source of a polychromatic beam of electromagnetic radiation comprises:

a. at least a first Xenon source of polychromatic electromagnetic radiation; and b. at least a first electromagnetic beam combining means;

said at least a first electromagnetic beam combining means being positioned with respect to said first Xenon source of polychromatic electromagnetic radiation such that a beam of polychromatic electromagnetic radiation from said first Xenon source of polychromatic electromagnetic radiation passes through said at least a first electromagnetic beam combining means, and such that another beam of polychromatic electromagnetic radiation from said first Xenon source of polychromatic electromagnetic radiation reflects from said at least a first electromagnetic beam combining means and is commingled with said beam of polychromatic electromagnetic radiation from said first Xenon source of polychromatic electromagnetic radiation which passes through said at least a first electromagnetic beam combining means, said resultant beam of polychromatic electromagnetic radiation substantially being said output beam of polychromatic electromagnetic radiation which has an increased UV/deep UV intensity;

said system for providing an output beam of polychromatic electromagnetic radiation which has a relatively broad and flattened intensity vs. wavelength characteristic over a wavelength spectrum being optionally further characterized by a selection from the group consisting of:

a1. a. a third beam from said source of electromagnetic radiation; and b. a second electromagnetic beam combining means;

said second electromagnetic beam combining means being positioned with respect to said commingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means, said second electromagnetic beam combining means being also positioned with respect to said third beam of polychromatic electromagnetic radiation provided by said first Xenon source such that a beam of electromagnetic radiation from said third beam of polychromatic electromagnetic radiation reflects from said second electromagnetic beam combining means such that a second resultant beam of polychromatic electromagnetic radiation which is substantially an output beam of polychromatic electromagnetic radiation which has a relatively even more UV/deep UV intensity comprising said commingled composite of a plurality of input beams of polychromatic electromagnetic radiation of said first, second and third beams, which first source; and a3. there being present in the pathway of at least one of said beams from said at least on Xenon source a means for attenuating the intensity of wavelengths other than at UV/deep UV.

27. A material system investigation system comprising at least one Xenon source of a polychromatic beam of electromagnetic radiation, a material system supporting stage, a detector, and a processor for performing calculations that evaluate detector output signal;

there optionally being present a polarizer between said source and said material system supporting stage, an analyzer between said material system supporting stage and said detector, and optionally at least one compensator between said polarizer and analyzer;

such that in use said Xenon source of a polychromatic beam of electromagnetic radiation is caused to provide a beam of electromagnetic radiation and direct it to interact with a sample which is placed on said material system supporting stage after optionally passing through said polarizer and analyzer and at least one compensator, and into said detector which in turn produces data corresponding to a parameter vs. at least one selection from the group consisting of:

angle-of-incidence; and wavelength;

including mathematical equivalents thereof;

said material system investigation system being characterized in that said source of a polychromatic beam of electromagnetic radiation comprises only at least one Xenon arc lamp which is used to provide UV/deep UV wavelength electromagnetic radiation without application of a supplemental source of electromagnetic radiation, in optional combination with a means for attenuating the intensity of other wavelengths;

which material system investigation system further comprises a back-reflector having a reflective surface;

said back-reflector being situated with respect to said at least one Xenon source of electromagnetic radiation such that at least some electromagnetic radiation emitted in a direction other than that of the beam of electromagnetic radiation, is redirected into the direction of said beam of electromagnetic radiation thereby;

said system being optionally characterized in that said back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

28. A material system investigation system comprising at least one Xenon source of a polychromatic beam of electromagnetic radiation, a material system supporting stage, a detector, and a processor for performing calculations that evaluate detector output signal;

there optionally being present a polarizer between said source and said material system supporting stage, an analyzer between said material system supporting stage and said detector, and optionally at least one compensator between said polarizer and analyzer;

such that in use said Xenon source of a polychromatic beam of electromagnetic radiation is caused to provide a beam of electromagnetic radiation and direct it to interact with a sample which is placed on said material system supporting stage after optionally passing through said polarizer and analyzer and at least one compensator, and into said detector which in turn produces data corresponding to a parameter vs. at least one selection from the group consisting of:

angle-of-incidence; and wavelength;

including mathematical equivalents thereof;

said material system investigation system being characterized in that said source of a polychromatic beam of electromagnetic radiation comprises only at least one Xenon arc lamp which is used to provide UV/deep UV wavelength electromagnetic radiation without application of a supplemental source of electromagnetic radiation, in optional combination with a means for attenuating the intensity of other wavelengths;

in which material system investigation system said at least one Xenon arc-lamp presents with an elongated dimension, said Xenon arc-lamp being oriented such that its elongated dimension projects substantially horizontally;

said system further comprising means for implementing a selection from the group consisting of:

controlling the vertical location of said Xenon source and a reflective means and means for controlling the rotation of said reflective means, such that in use a beam of electromagnetic beam is produced by said arc-lamp and directed out the lower surface thereof onto said reflective means, which reflectively directs it at an angle-of-incidence onto a sample surface; and controlling the vertical location of a reflective means and means for controlling the rotation and vertical location thereof, such that in use a beam of electromagnetic beam is produced by said arc-lamp and directed out the lower surface thereof onto said reflective means, which reflectively directs it at an angle-of-incidence onto a sample surface.

* * * * *